(12) United States Patent
Stevenson et al.

(10) Patent No.: US 11,026,688 B2
(45) Date of Patent: Jun. 8, 2021

(54) FOLDED BUTTRESS FOR USE WITH A SURGICAL APPARATUS

(71) Applicant: Covidien LP, Mansfield, MA (US)

(72) Inventors: Richard Stevenson, Colchester, CT (US); Paul Scirica, Huntington, CT (US)

(73) Assignee: COVIDIEN LP, Mansfield, MA (US)

( * ) Notice: Subject to any disclaimer, the term of this patent is extended or adjusted under 35 U.S.C. 154(b) by 185 days.

(21) Appl. No.: 16/436,981

(22) Filed: Jun. 11, 2019

(65) Prior Publication Data

US 2019/0290280 A1    Sep. 26, 2019

Related U.S. Application Data

(63) Continuation of application No. 15/201,952, filed on Jul. 5, 2016, now Pat. No. 10,349,942, which is a
(Continued)

(51) Int. Cl.
| | |
|---|---|
| *A61B 17/10* | (2006.01) |
| *A61B 17/072* | (2006.01) |
| *A61B 17/068* | (2006.01) |

(52) U.S. Cl.
CPC .......... *A61B 17/105* (2013.01); *A61B 17/068* (2013.01); *A61B 17/072* (2013.01);
(Continued)

(58) Field of Classification Search
CPC ... A61B 17/105; A61B 17/068; A61B 17/072; A61B 17/07207; A61B 17/07292;
(Continued)

(56) References Cited

U.S. PATENT DOCUMENTS 3,054,406 A  9/1962 Usher
3,079,606 A  3/1963 Bobrov et al.
(Continued)

FOREIGN PATENT DOCUMENTS

CA  2282761 A1  9/1998
CA  2 667 434 A1  5/2008
(Continued)

OTHER PUBLICATIONS

European Office Action corresponding to counterpart Int'l Appln. No. EP 14 17 2681.0 dated May 13, 2016.
(Continued)

*Primary Examiner* — Robert F Long
*Assistant Examiner* — Xavier A Madison

(57) ABSTRACT

An end effector for use with a surgical apparatus. The end effector comprising a staple cartridge having a tissue contacting surface defining a central longitudinal slot and an anvil plate having a tissue contacting surface defining a central longitudinal slot. A folded surgical buttress configured to overlie each of the tissue contacting surfaces of the staple cartridge and anvil plate and configured to retain the surgical buttress to the tissue contacting surfaces of each of the staple cartridge and anvil plate. The surgical buttress having a first longitudinal portion, a second longitudinal portion, and middle longitudinal portion between the first and second longitudinal portions, wherein the middle longitudinal portion is folded and configured to fit within the central longitudinal slot of each of the staple cartridge and anvil plate.

18 Claims, 5 Drawing Sheets

Related U.S. Application Data continuation of application No. 13/713,261, filed on Dec. 13, 2012, now Pat. No. 9,402,627.

(52) U.S. Cl.
CPC .. *A61B 17/07207* (2013.01); *A61B 17/07292* (2013.01); *A61B 2017/07257* (2013.01); *A61B 2017/07271* (2013.01); *A61B 2017/07285* (2013.01)

(58) Field of Classification Search
CPC ........... A61B 2017/07257; A61B 2017/07271; A61B 2017/07285
USPC .......................................... 227/175.1–182.1
See application file for complete search history.

(56) References Cited

U.S. PATENT DOCUMENTS

| | | |
|---|---|---|
| 3,124,136 A | 3/1964 | Usher |
| 3,490,675 A | 1/1970 | Green et al. |
| 3,499,591 A | 3/1970 | Green |
| 3,797,494 A | 3/1974 | Zaffaroni |
| 4,347,847 A | 9/1982 | Usher |
| 4,354,628 A | 10/1982 | Green |
| 4,429,695 A | 2/1984 | Green |
| 4,452,245 A | 6/1984 | Usher |
| 4,605,730 A | 8/1986 | Shalaby et al. |
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,065,929 A | 11/1991 | Schulze et al. |
| 5,112,496 A | 5/1992 | Dhawan et al. |
| 5,205,459 A | 4/1993 | Brinkerhoff et al. |
| 5,263,629 A | 11/1993 | Trumbull et al. |
| 5,281,197 A | 1/1994 | Arias et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,503,638 A | 4/1996 | Cooper et al. |
| 5,542,594 A | 8/1996 | McKean et al. |
| 5,549,628 A | 8/1996 | Cooper et al. |
| 5,575,803 A | 11/1996 | Cooper et al. |
| 5,645,915 A | 7/1997 | Kranzler et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,833,695 A | 11/1998 | Yoon |
| 5,843,096 A | 12/1998 | Igaki et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,957,363 A | 9/1999 | Heck |
| 5,964,394 A | 10/1999 | Robertson |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,099,551 A | 8/2000 | Gabbay |
| 6,142,933 A | 11/2000 | Longo et al. |
| 6,149,667 A | 11/2000 | Hovland et al. |
| 6,155,265 A | 12/2000 | Hammerslag |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,270,530 B1 | 8/2001 | Eldridge et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,330,965 B1 | 12/2001 | Milliman et al. |
| 6,436,030 B2 | 8/2002 | Rehil |
| 6,454,780 B1 | 9/2002 | Wallace |
| 6,461,368 B2 | 10/2002 | Fogarty et al. |
| 6,503,257 B2 | 1/2003 | Grant et al. |
| 6,514,283 B2 | 2/2003 | DiMatteo et al. |
| 6,517,566 B1 | 2/2003 | Hovland et al. |
| 6,551,356 B2 | 4/2003 | Rousseau |
| 6,568,398 B2 | 5/2003 | Cohen |
| 6,592,597 B2 | 7/2003 | Grant et al. |
| 6,610,006 B1 | 8/2003 | Amid et al. |
| 6,638,285 B2 | 10/2003 | Gabbay |
| 6,652,594 B2 | 11/2003 | Francis et al. |
| 6,656,193 B2 | 12/2003 | Grant et al. |
| 6,669,735 B1 | 12/2003 | Pelissier |
| 6,677,258 B2 | 1/2004 | Carroll et al. |
| 6,685,714 B2 | 2/2004 | Rousseau |
| 6,702,828 B2 | 3/2004 | Whayne |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,773,458 B1 | 8/2004 | Brauker et al. |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,959,851 B2 | 11/2005 | Heinrich |
| 7,025,772 B2 | 4/2006 | Gellman et al. |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,253 B2 | 10/2006 | Mastri et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,179,268 B2 | 2/2007 | Roy et al. |
| 7,232,449 B2 | 6/2007 | Sharkawy et al. |
| 7,241,300 B2 | 7/2007 | Sharkawy et al. |
| 7,307,031 B2 | 12/2007 | Carroll et al. |
| 7,311,720 B2 | 12/2007 | Mueller et al. |
| 7,334,717 B2 | 2/2008 | Rethy et al. |
| 7,377,928 B2 | 5/2008 | Zubik et al. |
| 7,434,717 B2 | 10/2008 | Shelton, IV et al. |

(56) References Cited

U.S. PATENT DOCUMENTS

| | | | |
|---|---|---|---|
| 7,438,209 | B1 | 10/2008 | Hess et al. |
| 7,547,312 | B2 | 6/2009 | Bauman et al. |
| 7,559,937 | B2 | 7/2009 | de la Torre et al. |
| 7,571,845 | B2 | 8/2009 | Viola |
| 7,594,921 | B2 | 9/2009 | Browning |
| 7,604,151 | B2 | 10/2009 | Hess et al. |
| 7,665,646 | B2 | 2/2010 | Prommersberger |
| 7,666,198 | B2 | 2/2010 | Suyker et al. |
| 7,669,747 | B2 | 3/2010 | Weisenburgh, II et al. |
| 7,717,313 | B2 | 5/2010 | Criscuolo et al. |
| 7,722,642 | B2 | 5/2010 | Williamson, IV et al. |
| 7,744,627 | B2 | 6/2010 | Orban, III et al. |
| 7,776,060 | B2 | 8/2010 | Mooradian et al. |
| 7,789,889 | B2 | 9/2010 | Zubik et al. |
| 7,793,813 | B2 | 9/2010 | Bettuchi |
| 7,799,026 | B2 | 9/2010 | Schechter et al. |
| 7,823,592 | B2 | 11/2010 | Bettuchi et al. |
| 7,824,420 | B2 | 11/2010 | Eldridge et al. |
| 7,845,533 | B2 | 12/2010 | Marczyk et al. |
| 7,845,536 | B2 | 12/2010 | Viola et al. |
| 7,846,149 | B2 | 12/2010 | Jankowski |
| 7,892,247 | B2 | 2/2011 | Conston et al. |
| 7,909,224 | B2 | 3/2011 | Prommersberger |
| 7,909,837 | B2 | 3/2011 | Crews et al. |
| 7,938,307 | B2 | 5/2011 | Bettuchi |
| 7,942,890 | B2 | 5/2011 | D'Agostino et al. |
| 7,950,561 | B2 | 5/2011 | Aranyi |
| 7,951,166 | B2 | 5/2011 | Orban, III et al. |
| 7,967,179 | B2 | 6/2011 | Olson et al. |
| 7,988,027 | B2 * | 8/2011 | Olson ............... A61B 17/07292 227/175.1 |
| 8,011,550 | B2 | 9/2011 | Aranyi et al. |
| 8,016,177 | B2 | 9/2011 | Bettuchi et al. |
| 8,016,178 | B2 | 9/2011 | Olson et al. |
| 8,025,199 | B2 | 9/2011 | Whitman et al. |
| 8,028,883 | B2 | 10/2011 | Stopek |
| 8,033,983 | B2 | 10/2011 | Chu et al. |
| 8,062,330 | B2 | 11/2011 | Prommersberger et al. |
| 8,083,119 | B2 | 12/2011 | Prommersberger |
| 8,123,766 | B2 | 2/2012 | Bauman et al. |
| 8,123,767 | B2 | 2/2012 | Bauman et al. |
| 8,133,336 | B2 | 3/2012 | Kettlewell et al. |
| 8,133,559 | B2 | 3/2012 | Lee et al. |
| 8,146,791 | B2 | 4/2012 | Bettuchi et al. |
| 8,157,149 | B2 | 4/2012 | Olson et al. |
| 8,157,151 | B2 | 4/2012 | Ingmanson et al. |
| 8,167,895 | B2 | 5/2012 | D'Agostino et al. |
| 8,178,746 | B2 | 5/2012 | Hildeberg et al. |
| 8,192,460 | B2 | 6/2012 | Orban, III et al. |
| 8,210,414 | B2 | 7/2012 | Bettuchi et al. |
| 8,225,799 | B2 | 7/2012 | Bettuchi |
| 8,225,981 | B2 | 7/2012 | Criscuolo et al. |
| 8,231,043 | B2 | 7/2012 | Tarinelli et al. |
| 8,235,273 | B2 | 8/2012 | Olson et al. |
| 8,245,901 | B2 | 8/2012 | Stopek |
| 8,256,654 | B2 | 9/2012 | Bettuchi et al. |
| 8,257,391 | B2 | 9/2012 | Orban, III et al. |
| 8,276,800 | B2 | 10/2012 | Bettuchi |
| 8,286,849 | B2 | 10/2012 | Bettuchi |
| 8,308,042 | B2 | 11/2012 | Aranyi |
| 8,308,045 | B2 | 11/2012 | Bettuchi et al. |
| 8,308,046 | B2 | 11/2012 | Prommersberger |
| 8,312,885 | B2 | 11/2012 | Bettuchi et al. |
| 8,313,014 | B2 | 11/2012 | Bettuchi |
| 8,322,590 | B2 | 12/2012 | Patel et al. |
| 8,348,126 | B2 | 1/2013 | Olson et al. |
| 8,348,130 | B2 | 1/2013 | Shah et al. |
| 8,365,972 | B2 | 2/2013 | Aranyi et al. |
| 8,371,491 | B2 | 2/2013 | Huitema et al. |
| 8,371,492 | B2 | 2/2013 | Aranyi et al. |
| 8,371,493 | B2 | 2/2013 | Aranyi et al. |
| 8,393,514 | B2 | 3/2013 | Shelton, IV et al. |
| 8,393,517 | B2 | 3/2013 | Milo |
| 8,408,440 | B2 | 4/2013 | Olson et al. |
| 8,413,869 | B2 | 4/2013 | Heinrich |
| 8,413,871 | B2 | 4/2013 | Racenet et al. |
| 8,424,742 | B2 | 4/2013 | Bettuchi |
| 8,453,652 | B2 | 6/2013 | Stopek |
| 8,453,904 | B2 | 6/2013 | Eskaros et al. |
| 8,453,909 | B2 | 6/2013 | Olson et al. |
| 8,453,910 | B2 | 6/2013 | Bettuchi et al. |
| 8,464,925 | B2 | 6/2013 | Hull et al. |
| 8,474,677 | B2 | 7/2013 | Woodard, Jr. et al. |
| 8,479,968 | B2 | 7/2013 | Hodgkinson et al. |
| 8,485,414 | B2 | 7/2013 | Criscuolo et al. |
| 8,496,683 | B2 | 7/2013 | Prommersberger et al. |
| 8,511,533 | B2 | 8/2013 | Viola et al. |
| 8,512,402 | B2 | 8/2013 | Marczyk et al. |
| 8,529,600 | B2 | 9/2013 | Woodard, Jr. et al. |
| 8,540,131 | B2 | 9/2013 | Swayze |
| 8,551,138 | B2 | 10/2013 | Orban, III et al. |
| 8,556,918 | B2 | 10/2013 | Bauman et al. |
| 8,561,873 | B2 | 10/2013 | Ingmanson et al. |
| 8,579,990 | B2 | 11/2013 | Priewe |
| 8,584,920 | B2 | 11/2013 | Hodgkinson |
| 8,590,762 | B2 | 11/2013 | Hess et al. |
| 8,616,430 | B2 | 12/2013 | Stopek et al. |
| 8,631,989 | B2 | 1/2014 | Aranyi et al. |
| 8,646,674 | B2 | 2/2014 | Schulte et al. |
| 8,668,129 | B2 | 3/2014 | Olson |
| 8,684,250 | B2 | 4/2014 | Bettuchi et al. |
| 8,721,703 | B2 | 5/2014 | Fowler |
| 8,757,466 | B2 | 6/2014 | Olson et al. |
| 8,789,737 | B2 | 7/2014 | Hodgkinson et al. |
| 8,814,888 | B2 | 8/2014 | Sgro |
| 8,820,606 | B2 | 9/2014 | Hodgkinson |
| 8,857,694 | B2 | 10/2014 | Shelton, IV et al. |
| 8,864,009 | B2 | 10/2014 | Shelton, IV et al. |
| 8,870,050 | B2 | 10/2014 | Hodgkinson |
| 8,920,443 | B2 | 12/2014 | Hiles et al. |
| 8,920,444 | B2 | 12/2014 | Hiles et al. |
| 8,939,344 | B2 | 1/2015 | Olson et al. |
| 8,967,448 | B2 | 3/2015 | Carter et al. |
| 9,005,243 | B2 | 4/2015 | Stopek et al. |
| 9,010,606 | B2 | 4/2015 | Aranyi et al. |
| 9,010,608 | B2 | 4/2015 | Casasanta, Jr. et al. |
| 9,010,609 | B2 | 4/2015 | Carter et al. |
| 9,010,610 | B2 | 4/2015 | Hodgkinson |
| 9,010,612 | B2 | 4/2015 | Stevenson et al. |
| 9,016,543 | B2 | 4/2015 | Stopek et al. |
| 9,016,544 | B2 | 4/2015 | Hodgkinson et al. |
| 9,044,227 | B2 | 6/2015 | Shelton, IV et al. |
| 9,055,944 | B2 | 6/2015 | Hodgkinson et al. |
| 9,084,602 | B2 | 7/2015 | Gleiman |
| 9,107,665 | B2 | 8/2015 | Hodgkinson et al. |
| 9,107,667 | B2 | 8/2015 | Hodgkinson |
| 9,113,873 | B2 | 8/2015 | Marczyk et al. |
| 9,113,885 | B2 | 8/2015 | Hodgkinson et al. |
| 9,113,893 | B2 | 8/2015 | Sorrentino et al. |
| 9,161,753 | B2 | 10/2015 | Prior |
| 9,161,757 | B2 | 10/2015 | Bettuchi |
| 9,186,140 | B2 | 11/2015 | Hiles et al. |
| 9,186,144 | B2 | 11/2015 | Stevenson et al. |
| 9,192,378 | B2 | 11/2015 | Aranyi et al. |
| 9,192,379 | B2 | 11/2015 | Aranyi et al. |
| 9,192,383 | B2 | 11/2015 | Milliman |
| 9,192,384 | B2 | 11/2015 | Bettuchi |
| 9,198,660 | B2 | 12/2015 | Hodgkinson |
| 9,198,663 | B1 | 12/2015 | Marczyk et al. |
| 9,204,881 | B2 | 12/2015 | Penna |
| 9,220,504 | B2 | 12/2015 | Viola et al. |
| 9,226,754 | B2 | 1/2016 | D'Agostino et al. |
| 9,237,893 | B2 | 1/2016 | Carter et al. |
| 9,277,922 | B2 | 3/2016 | Carter et al. |
| 9,295,466 | B2 | 3/2016 | Hodgkinson et al. |
| 9,326,773 | B2 | 5/2016 | Casasanta, Jr. et al. |
| 9,328,111 | B2 | 5/2016 | Zhou et al. |
| 9,345,479 | B2 | 5/2016 | Racenet et al. |
| 9,351,729 | B2 | 5/2016 | Orban, III et al. |
| 9,351,731 | B2 | 5/2016 | Carter et al. |
| 9,351,732 | B2 | 5/2016 | Hodgkinson |
| 9,358,005 | B2 | 6/2016 | Shelton, IV et al. |
| 9,364,229 | B2 | 6/2016 | D'Agostino et al. |
| 9,402,627 | B2 | 8/2016 | Stevenson et al. |

(56) References Cited

U.S. PATENT DOCUMENTS

| | | |
|---|---|---|
| 9,414,839 B2 | 8/2016 | Penna |
| 9,433,412 B2 | 9/2016 | Bettuchi et al. |
| 9,433,413 B2 | 9/2016 | Stopek |
| 9,433,420 B2 | 9/2016 | Hodgkinson |
| 9,445,812 B2 | 9/2016 | Olson et al. |
| 9,445,817 B2 | 9/2016 | Bettuchi |
| 9,486,215 B2 | 11/2016 | Olson et al. |
| 9,504,470 B2 | 11/2016 | Willman |
| 9,572,576 B2 | 2/2017 | Hodgkinson et al. |
| 9,597,077 B2 | 3/2017 | Hodgkinson |
| 9,610,080 B2 | 4/2017 | Whitfield et al. |
| 9,622,745 B2 | 4/2017 | Ingmanson et al. |
| 9,629,626 B2 | 4/2017 | Soltz et al. |
| 9,655,620 B2 | 5/2017 | Prescott et al. |
| 9,675,351 B2 | 6/2017 | Hodgkinson et al. |
| 9,681,936 B2 | 6/2017 | Hodgkinson et al. |
| 9,693,772 B2 | 7/2017 | Ingmanson et al. |
| 9,775,617 B2 | 10/2017 | Carter et al. |
| 9,775,618 B2 | 10/2017 | Bettuchi et al. |
| 9,782,173 B2 | 10/2017 | Mozdzierz |
| 9,844,378 B2 | 12/2017 | Casasanta et al. |
| 9,931,116 B2 | 4/2018 | Racenet et al. |
| 10,022,125 B2 | 7/2018 | Stopek et al. |
| 10,349,942 B2 | 7/2019 | Stevenson et al. |
| 2002/0028243 A1 | 3/2002 | Masters |
| 2002/0091397 A1 | 7/2002 | Chen |
| 2002/0165559 A1 | 11/2002 | Grant et al. |
| 2003/0065345 A1 | 4/2003 | Weadock |
| 2003/0083676 A1 | 5/2003 | Wallace |
| 2003/0120284 A1 | 6/2003 | Palacios et al. |
| 2003/0125676 A1 | 7/2003 | Swenson et al. |
| 2003/0181927 A1 | 9/2003 | Wallace |
| 2003/0183671 A1 | 10/2003 | Mooradian et al. |
| 2003/0208231 A1 | 11/2003 | Williamson et al. |
| 2004/0092912 A1 | 5/2004 | Jinno et al. |
| 2004/0107006 A1 | 6/2004 | Francis et al. |
| 2004/0131418 A1 | 7/2004 | Budde et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0143756 A1 | 6/2005 | Jankowski |
| 2005/0149073 A1 | 7/2005 | Arani et al. |
| 2005/0228446 A1 | 10/2005 | Mooradian et al. |
| 2005/0283256 A1 | 12/2005 | Sommerich et al. |
| 2006/0004407 A1 | 1/2006 | Hiles et al. |
| 2006/0025816 A1 | 2/2006 | Shelton |
| 2006/0085034 A1 | 4/2006 | Bettuchi |
| 2006/0135992 A1 | 6/2006 | Bettuchi et al. |
| 2006/0173470 A1 | 8/2006 | Oray et al. |
| 2006/0178683 A1 | 8/2006 | Shimoji et al. |
| 2006/0190027 A1 | 8/2006 | Downey |
| 2006/0219752 A1 | 10/2006 | Arad et al. |
| 2006/0271104 A1 | 11/2006 | Viola et al. |
| 2007/0026031 A1 | 2/2007 | Bauman et al. |
| 2007/0034669 A1 | 2/2007 | de la Torre et al. |
| 2007/0049953 A2 | 3/2007 | Shimoji et al. |
| 2007/0123839 A1 | 5/2007 | Rousseau et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0243227 A1 | 10/2007 | Gertner |
| 2007/0246505 A1 | 10/2007 | Pace-Floridia et al. |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0200949 A1 | 8/2008 | Hiles et al. |
| 2008/0220047 A1 | 9/2008 | Sawhney et al. |
| 2008/0230583 A1 | 9/2008 | Heinrich |
| 2008/0290134 A1 | 11/2008 | Bettuchi et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0030452 A1 | 1/2009 | Bauman et al. |
| 2009/0031842 A1 | 2/2009 | Kawai et al. |
| 2009/0043334 A1 | 2/2009 | Bauman et al. |
| 2009/0076510 A1 | 3/2009 | Bell et al. |
| 2009/0076528 A1 | 3/2009 | Sgro |
| 2009/0078739 A1 | 3/2009 | Viola |
| 2009/0095791 A1 | 4/2009 | Eskaros et al. |
| 2009/0095792 A1 | 4/2009 | Bettuchi |
| 2009/0120994 A1 | 5/2009 | Murray et al. |
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0218384 A1 | 9/2009 | Aranyi |
| 2009/0277944 A9 | 11/2009 | Dalessandro et al. |
| 2009/0277947 A1 | 11/2009 | Viola |
| 2009/0287230 A1 | 11/2009 | D'Agostino et al. |
| 2010/0012704 A1 | 1/2010 | Tarinelli Racenet et al. |
| 2010/0016855 A1 | 1/2010 | Ramstein et al. |
| 2010/0065606 A1 | 3/2010 | Stopek |
| 2010/0065607 A1 | 3/2010 | Orban, III et al. |
| 2010/0072254 A1 | 3/2010 | Aranyi et al. |
| 2010/0147921 A1 | 6/2010 | Olson |
| 2010/0147922 A1 | 6/2010 | Olson |
| 2010/0147923 A1 | 6/2010 | D'Agostino et al. |
| 2010/0174253 A1 | 7/2010 | Cline et al. |
| 2010/0243707 A1 | 9/2010 | Olson et al. |
| 2010/0243708 A1 | 9/2010 | Aranyi |
| 2010/0243711 A1 | 9/2010 | Olson et al. |
| 2010/0249805 A1 | 9/2010 | Olson et al. |
| 2010/0264195 A1 | 10/2010 | Bettuchi |
| 2010/0282815 A1 | 11/2010 | Bettuchi et al. |
| 2010/0331859 A1 | 12/2010 | Omori |
| 2010/0331880 A1 | 12/2010 | Stopek |
| 2011/0024476 A1 | 2/2011 | Bettuchi et al. |
| 2011/0024481 A1 | 2/2011 | Bettuchi et al. |
| 2011/0034910 A1 | 2/2011 | Ross et al. |
| 2011/0036894 A1 | 2/2011 | Bettuchi |
| 2011/0042442 A1 | 2/2011 | Viola et al. |
| 2011/0046650 A1 | 2/2011 | Bettuchi |
| 2011/0057016 A1 | 3/2011 | Bettuchi |
| 2011/0087279 A1 | 4/2011 | Shah et al. |
| 2011/0089220 A1 | 4/2011 | Ingmanson et al. |
| 2011/0125138 A1 | 5/2011 | Malinouskas et al. |
| 2011/0166673 A1 | 7/2011 | Patel et al. |
| 2011/0215132 A1 | 9/2011 | Aranyi et al. |
| 2011/0278346 A1 | 11/2011 | Hull et al. |
| 2011/0278347 A1 | 11/2011 | Olson et al. |
| 2012/0074199 A1 | 3/2012 | Olson et al. |
| 2012/0080336 A1 | 4/2012 | Shelton, IV et al. |
| 2012/0083723 A1 | 4/2012 | Vitaris et al. |
| 2012/0145767 A1 | 6/2012 | Shah et al. |
| 2012/0187179 A1 | 7/2012 | Gleiman |
| 2012/0197272 A1 | 8/2012 | Oray et al. |
| 2012/0241491 A1 | 9/2012 | Aldridge et al. |

(56) References Cited

U.S. PATENT DOCUMENTS

| | | |
|---|---|---|
| 2012/0241499 A1 | 9/2012 | Baxter, III et al. |
| 2012/0253298 A1 | 10/2012 | Henderson et al. |
| 2012/0273547 A1 | 11/2012 | Hodgkinson et al. |
| 2013/0037596 A1 | 2/2013 | Bear et al. |
| 2013/0105548 A1 | 5/2013 | Hodgkinson et al. |
| 2013/0105553 A1 | 5/2013 | Racenet et al. |
| 2013/0112732 A1 | 5/2013 | Aranyi et al. |
| 2013/0112733 A1 | 5/2013 | Aranyi et al. |
| 2013/0123816 A1 | 5/2013 | Hodgkinson et al. |
| 2013/0146641 A1 | 6/2013 | Shelton, IV et al. |
| 2013/0153633 A1 | 6/2013 | Casasanta, Jr. et al. |
| 2013/0153634 A1 | 6/2013 | Carter et al. |
| 2013/0153635 A1 | 6/2013 | Hodgkinson |
| 2013/0153636 A1 | 6/2013 | Shelton, IV et al. |
| 2013/0153638 A1 | 6/2013 | Carter et al. |
| 2013/0153639 A1 | 6/2013 | Hodgkinson et al. |
| 2013/0153640 A1 | 6/2013 | Hodgkinson |
| 2013/0153641 A1 | 6/2013 | Shelton, IV et al. |
| 2013/0161374 A1 | 6/2013 | Swayze et al. |
| 2013/0181031 A1 | 7/2013 | Olson et al. |
| 2013/0193186 A1 | 8/2013 | Racenet et al. |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0209659 A1 | 8/2013 | Racenet et al. |
| 2013/0221062 A1 | 8/2013 | Hodgkinson |
| 2013/0240600 A1 | 9/2013 | Bettuchi |
| 2013/0240601 A1 | 9/2013 | Bettuchi et al. |
| 2013/0240602 A1 | 9/2013 | Stopek |
| 2013/0256380 A1 | 10/2013 | Schmid et al. |
| 2013/0277411 A1 | 10/2013 | Hodgkinson et al. |
| 2013/0306707 A1 | 11/2013 | Viola et al. |
| 2013/0310873 A1 | 11/2013 | Stopek et al. |
| 2013/0327807 A1 | 12/2013 | Olson et al. |
| 2014/0012317 A1 | 1/2014 | Orban et al. |
| 2014/0021242 A1 | 1/2014 | Hodgkinson et al. |
| 2014/0027490 A1 | 1/2014 | Marczyk et al. |
| 2014/0034704 A1 | 2/2014 | Ingmanson et al. |
| 2014/0048580 A1 | 2/2014 | Merchant et al. |
| 2014/0061280 A1 | 3/2014 | Ingmanson et al. |
| 2014/0061281 A1 | 3/2014 | Hodgkinson |
| 2014/0084042 A1 | 3/2014 | Stopek et al. |
| 2014/0097224 A1 | 4/2014 | Prior |
| 2014/0117066 A1 | 5/2014 | Aranyi et al. |
| 2014/0130330 A1 | 5/2014 | Olson et al. |
| 2014/0131418 A1 | 5/2014 | Kostrzewski |
| 2014/0131419 A1 | 5/2014 | Bettuchi |
| 2014/0138423 A1 | 5/2014 | Whitfield et al. |
| 2014/0151431 A1 | 6/2014 | Hodgkinson et al. |
| 2014/0155916 A1 | 6/2014 | Hodgkinson et al. |
| 2014/0158742 A1 | 6/2014 | Stopek et al. |
| 2014/0166721 A1 | 6/2014 | Stevenson et al. |
| 2014/0197224 A1 | 7/2014 | Penna |
| 2014/0203061 A1 | 7/2014 | Hodgkinson |
| 2014/0217147 A1 | 8/2014 | Milliman |
| 2014/0217148 A1 | 8/2014 | Penna |
| 2014/0239046 A1 | 8/2014 | Milliman |
| 2014/0239047 A1 | 8/2014 | Hodgkinson et al. |
| 2014/0252062 A1 | 9/2014 | Mozdzierz |
| 2015/0001276 A1 | 1/2015 | Hodgkinson et al. |
| 2015/0041347 A1 | 2/2015 | Hodgkinson |
| 2015/0097018 A1 | 4/2015 | Hodgkinson |
| 2015/0115015 A1 | 4/2015 | Prescott et al. |
| 2015/0122872 A1 | 5/2015 | Olson et al. |
| 2015/0133995 A1 | 5/2015 | Shelton, IV et al. |
| 2015/0164503 A1 | 6/2015 | Stevenson et al. |
| 2015/0164506 A1 | 6/2015 | Carter et al. |
| 2015/0164507 A1 | 6/2015 | Carter et al. |
| 2015/0196297 A1 | 7/2015 | Stopek et al. |
| 2015/0209033 A1 | 7/2015 | Hodgkinson |
| 2015/0209045 A1 | 7/2015 | Hodgkinson et al. |
| 2015/0209048 A1 | 7/2015 | Carter et al. |
| 2015/0231409 A1 | 8/2015 | Racenet et al. |
| 2015/0305743 A1 | 10/2015 | Casasanta et al. |
| 2015/0327864 A1 | 11/2015 | Hodgkinson et al. |
| 2016/0022268 A1 | 1/2016 | Prior |
| 2016/0045200 A1 | 2/2016 | Milliman |
| 2016/0058451 A1 | 3/2016 | Racenet et al. |
| 2016/0100834 A1 | 4/2016 | Viola et al. |
| 2016/0106430 A1 | 4/2016 | Carter et al. |
| 2016/0113647 A1 | 4/2016 | Hodgkinson |
| 2016/0157857 A1 | 6/2016 | Hodgkinson et al. |
| 2016/0174988 A1 | 6/2016 | D'Agostino et al. |
| 2016/0206315 A1 | 7/2016 | Olson |
| 2016/0220257 A1 | 8/2016 | Casasanta et al. |
| 2016/0249923 A1 | 9/2016 | Hodgkinson et al. |
| 2016/0256166 A1 | 9/2016 | Stopek et al. |
| 2016/0270793 A1 | 9/2016 | Carter et al. |
| 2016/0310143 A1 | 10/2016 | Bettuchi |
| 2016/0338704 A1 | 11/2016 | Penna |
| 2016/0367252 A1 | 12/2016 | Olson et al. |
| 2016/0367253 A1 | 12/2016 | Hodgkinson |
| 2016/0367257 A1 | 12/2016 | Stevenson et al. |
| 2017/0042540 A1 | 2/2017 | Olson et al. |
| 2017/0049452 A1 | 2/2017 | Milliman |
| 2017/0150967 A1 | 6/2017 | Hodgkinson et al. |
| 2017/0172575 A1 | 6/2017 | Hodgkinson |
| 2017/0231629 A1 | 8/2017 | Stopek et al. |
| 2017/0238931 A1 | 8/2017 | Prescott et al. |
| 2017/0281328 A1 | 10/2017 | Hodgkinson et al. |
| 2017/0296188 A1 | 10/2017 | Ingmanson et al. |
| 2017/0303952 A1* | 10/2017 | Nativ ............... A61B 17/07207 |
| 2017/0354415 A1 | 12/2017 | Casasanta, Jr. et al. |
| 2018/0125491 A1 | 5/2018 | Aranyi |
| 2018/0140301 A1 | 5/2018 | Milliman |
| 2018/0168654 A1 | 6/2018 | Hodgkinson et al. |
| 2018/0214147 A1 | 8/2018 | Merchant et al. |

FOREIGN PATENT DOCUMENTS

| | | |
|---|---|---|
| CN | 1386477 A | 12/2002 |
| CN | 101310680 A | 11/2008 |
| CN | 101332110 A | 12/2008 |
| CN | 101507637 A | 8/2009 |
| DE | 1602563 U | 3/1950 |
| DE | 19924311 A1 | 11/2000 |
| EP | 0327022 A2 | 8/1989 |
| EP | 0594148 A1 | 4/1994 |
| EP | 0667119 A1 | 8/1995 |
| EP | 1064883 A1 | 1/2001 |
| EP | 1256317 A2 | 11/2002 |
| EP | 1256318 A1 | 11/2002 |
| EP | 1520525 A1 | 4/2005 |
| EP | 1621141 A2 | 2/2006 |
| EP | 1702570 A1 | 9/2006 |
| EP | 1759640 A2 | 3/2007 |
| EP | 1815804 A2 | 8/2007 |
| EP | 1825820 A1 | 8/2007 |
| EP | 1929958 A2 | 6/2008 |
| EP | 1994890 A1 | 11/2008 |
| EP | 2005894 A2 | 12/2008 |
| EP | 2005895 A2 | 12/2008 |
| EP | 2039308 A2 | 3/2009 |
| EP | 2090231 A1 | 8/2009 |
| EP | 2090244 A2 | 8/2009 |
| EP | 2090252 A2 | 8/2009 |
| EP | 2163211 A2 | 3/2010 |
| EP | 2189121 A1 | 5/2010 |
| EP | 2236098 A2 | 10/2010 |
| EP | 2236099 A1 | 10/2010 |
| EP | 2258282 A2 | 12/2010 |
| EP | 2292276 A2 | 3/2011 |
| EP | 2311386 A2 | 4/2011 |
| EP | 2436348 A1 | 4/2012 |
| EP | 2462880 B1 | 6/2012 |
| EP | 2491867 A1 | 8/2012 |
| EP | 2497431 A1 | 9/2012 |
| EP | 2517637 A1 | 10/2012 |
| EP | 2586380 A1 | 5/2013 |
| EP | 2604195 A1 | 6/2013 |
| EP | 2604197 A2 | 6/2013 |
| EP | 2620105 A1 | 7/2013 |
| EP | 2620106 A2 | 7/2013 |
| EP | 2630922 A1 | 8/2013 |

(56) References Cited

FOREIGN PATENT DOCUMENTS

| | | | |
|---|---|---|---|
| EP | 2644125 | A2 | 10/2013 |
| EP | 2762091 | A2 | 8/2014 |
| EP | 2008595 | B1 | 4/2016 |
| EP | 2198787 | B1 | 3/2017 |
| JP | 2000166933 | A | 6/2000 |
| JP | 2002202213 | A | 7/2002 |
| JP | 2007124166 | A | 5/2007 |
| WO | 9005489 | A1 | 5/1990 |
| WO | 95/16221 | A1 | 6/1995 |
| WO | 9622055 | A1 | 7/1996 |
| WO | 9701989 | A1 | 1/1997 |
| WO | 9713463 | A1 | 4/1997 |
| WO | 9817180 | A1 | 4/1998 |
| WO | 9945849 | A1 | 9/1999 |
| WO | 0010456 | A1 | 3/2000 |
| WO | 0016684 | A1 | 3/2000 |
| WO | 03082126 | A1 | 10/2003 |
| WO | 03088845 | A2 | 10/2003 |
| WO | 03094743 | A1 | 11/2003 |
| WO | 03105698 | A2 | 12/2003 |
| WO | 2005079675 | A2 | 9/2005 |
| WO | 2006023578 | A2 | 3/2006 |
| WO | 2006044490 | A2 | 4/2006 |
| WO | 2006083748 | A1 | 8/2006 |
| WO | 2007121579 | A1 | 11/2007 |
| WO | 2008057281 | A2 | 5/2008 |
| WO | 2008109125 | A1 | 9/2008 |
| WO | 2010075298 | A2 | 7/2010 |
| WO | 2011143183 | A2 | 11/2011 |
| WO | 2012044848 | A1 | 4/2012 |

OTHER PUBLICATIONS

Chinese Office Action corresponding to counterpart Int'l Appln. No. CN 201210545228 dated Jun. 29, 2016.
Japanese Office Action corresponding to counterpart Int'l Appln. No. JP 2012-250058 dated Jun. 29, 2016.
European Office Action corresponding to counterpart Int'l Appln. No. EP 14 15 7997.9 dated Jun. 29, 2016.
Canadian Office Action corresponding to counterpart Int'l Appln. No. CA 2,712,617 dated Jun. 30, 2016.
Chinese First Office Action corresponding to counterpart Int'l Appln. No. CN 2013103036903 dated Jun. 30, 2016.
Australian Patent Examination Report No. 1 corresponding to counterpart Int'l Appln. No. AU 2012250278 dated Jul. 10, 2016.
Australian Patent Examination Report No. 1 corresponding to counterpart Int'l Appln. No. AU 2012244382 dated Jul. 10, 2016.
Japanese Office Action corresponding to counterpart Int'l Appln. No. JP 2012-255242 dated Jul. 26, 2016.
Japanese Office Action corresponding to counterpart Int'l Appln. No. JP 2012-268668 dated Jul. 27, 2016.
European Office Action corresponding to counterpart Int'l Appln. No. EP 14 15 2060.1 dated Aug. 4, 2016.
European Office Action corresponding to counterpart Int'l Appln. No. EP 12 16 5609.4 dated Aug. 5, 2016.
European Office Action corresponding to counterpart Int'l Appln. No. EP 15 15 2392.5 dated Aug. 8, 2016.
Japanese Office Action corresponding to counterpart Int'l Appln. No. JP 2013-003624 dated Aug. 25, 2016.
Australian Patent Examination Report No. 1 corresponding to counterpart Int'l Appln. No. AU 2012261752 dated Sep. 5, 2016.
Japanese Office Action corresponding to counterpart Int'l Appln. No. JP 2014-252703 dated Sep. 26, 2016.
European Office Action corresponding to counterpart Int'l Appln. No. EP 12 19 8776.2 dated Sep. 12, 2016.
Japanese Office Action corresponding to counterpart Int'l Appln. No. JP 2013-000321 dated Sep. 13, 2016.
Chinese Second Office Action corresponding to counterpart Int'l Appln. No. CN 201310353628.5 dated Sep. 26, 2016.
European Office Action corresponding to counterpart Int'l Appln. No. EP 12 15 2541.4 dated Sep. 27, 2016.
Australian Patent Examination Report No. 1 corresponding to counterpart Int'l Appln. No. AU 2012268923 dated Sep. 28, 2016.
Chinese First Office Action corresponding to counterpart Int'l Appln. No. CN 201310646606.8 dated Dec. 23, 2016.
Chinese First Office Action corresponding to counterpart Int'l Appln. No. CN 201410028462.4 dated Mar. 2, 2017.
Extended European Search Report corresponding to counterpart Int'l Appln. No. EP 16 19 6549.6 dated Mar. 17, 2017.
Australian Examination Report No. 1 corresponding to counterpart Int'l Appln. No. AU 2013206777 dated Feb. 1, 2017.
Australian Examination Report No. 1 corresponding to counterpart Int'l Appln. No. AU 2013206804 dated Mar. 21, 2017.
Japanese Office Action corresponding to counterpart Int'l Appln. No. JP 2013-000321 dated Jan. 4, 2017.
Japanese Office Action corresponding to counterpart Int'l Appln. No. JP 2013-175379 dated Mar. 1, 2017.
Chinese First Office Action corresponding to counterpart Int'l Appln. No. CN 2013107068710 dated Dec. 16, 2016.
Chinese First Office Action corresponding to counterpart Int'l Appln. No. CN 201410084070 dated Mar. 13, 2017.
Australian Examination Report No. 1 corresponding to counterpart Int'l Appln. No. AU 2014201008 dated May 23, 2017.
Extended European Search Report corresponding to counterpart Int'l Appln. No. EP 16 16 6367.9 dated Jan. 16, 2017.
Australian Examination Report No. 1 corresponding to counterpart Int'l Appln. No. AU 2013211499 dated May 4, 2017.
Chinese Second Office Action corresponding to counterpart Int'l Appln. No. CN 2013103036903 dated Feb. 23, 2017.
Japanese Office Action corresponding to counterpart Int'l Appln. No. JP 2013-147701 dated Mar. 21, 2017.
European Office Action corresponding to counterpart European Appln. No. EP 15 17 4146.9 dated May 15, 2017.
Japanese Office Action corresponding to counterpart Japanese Appln. No. JP 2013-154561 dated May 23, 2017.
European Office Action corresponding to counterpart European Appln. No. EP 12 19 4784.0 dated May 29, 2017.
Japanese Office Action corresponding to counterpart Japanese Appln. No. JP 2013-169083 dated May 31, 2017.
Australian Examination Report No. 1 corresponding to counterpart Australian Appln. No. AU 2013213767 dated Jun. 29, 2017.
Australian Examination Report No. 2 corresponding to counterpart Australian Appln. No. AU 2012261752 dated Jul. 7, 2017.
Australian Examination Report No. 1 corresponding to counterpart Australian Appln. No. AU 2013266989 dated Jul. 10, 2017.
Extended European Search Report corresponding to counterpart European Appln. No. EP 14 15 3609.4 dated Jul. 14, 2017.
Australian Examination Report No. 1 corresponding to counterpart Australian Appln. No. AU 2013234418 dated Jul. 14, 2017.
Extended European Search Report corresponding to counterpart European Appln. No. EP 14 15 3610.2 dated Jul. 17, 2017.
Australian Examination Report No. 1 corresponding to counterpart Australian Appln. No. AU 2014200109 dated Jul. 20, 2017.
Australian Examination Report No. 1 corresponding to counterpart Australian Appln. No. AU 2014200074 dated Jul. 20, 2017.
Japanese Office Action corresponding to counterpart Japanese Appln. No. JP 2013-250857 dated Aug. 17, 2017.
Japanese Office Action corresponding to counterpart Japanese Appln. No. JP 2013-229471 dated Aug. 17, 2017.
Australian Examination Report No. 1 corresponding to counterpart Australian Appln. No. AU 2014200793 dated Sep. 2, 2017.
Extended European Search Report corresponding to EP 14 16 9739.1, completed Aug. 19, 2014 and Aug. 29, 2014; (7 pp).
Extended European Search Report corresponding to EP 14 15 7997.9, completed Sep. 9, 2014 and dated Sep. 17, 2014; (8 pp).
Extended European Search Report corresponding to EP 14 16 8904.2, completed Sep. 10, 2014 and dated Sep. 18, 2014; (8 pp).
Extended European Search Report corresponding to EP 13 19 4995.0, completed Jun. 5, 2014 and dated Oct. 13, 2014; (10 pp).
Extended European Search Report corresponding to EP 13 15 4571.7, completed Oct. 10, 2014 and dated Oct. 20, 2014; (8 pp).
Extended European Search Report corresponding to EP 14 18 1125.7, completed Oct. 16, 2014 and dated Oct. 24, 2014; (7 pp).

(56) References Cited

OTHER PUBLICATIONS

Extended European Search Report corresponding to EP 14 18 1127.3, completed Oct. 16, 2014 and dated Nov. 10, 2014; (8 pp).
Extended European Search Report corresponding to EP 14 19 0419.3, completed Mar. 24, 2015 and dated Mar. 30, 2015; (6 pp).
Extended European Search Report corresponding to EP No. 12 19 1035.0, completed Jan. 11, 2013 and dated Jan. 18, 2013; 7 pages.
Extended European Search Report corresponding to EP No. 12 18 6175.1, completed Jan. 15, 2013 and dated Jan. 23, 2013; 7 pages.
Extended European Search Report corresponding to EP No. 12 19 1114.3, completed Jan. 23, 2013 and dated Jan. 31, 2013; 10 pages.
Extended European Search Report corresponding to EP No. 12 19 2224.9, completed Mar. 14, 2013 and dated Mar. 26, 2013; 8 pages.
Extended European Search Report corresponding to EP No. 12 19 6911.7, completed Apr. 18, 2013 and dated Apr. 24, 2013; 8 pages.
European Office Action corresponding to counterpart Int'l Appln No. EP 12 198 776.2 dated Apr. 7, 2015.
European Office Action corresponding to counterpart Int'l Appln No. EP 13 156 297.7 dated Apr. 10, 2015.
Australian Examination Report No. 1 corresponding to counterpart Int'l Appln No. AU 2011250822 dated May 18, 2015.
European Office Action corresponding to counterpart Int'l Appln No. EP 12 186 175.1 dated Jun. 1, 2015.
Chinese Office Action corresponding to counterpart Int'l Appln No. CN 201010517292.8 dated Jun. 2, 2015.
Extended European Search Report corresponding to counterpart Int'l Appin No. EP 14 17 48145 dated Jun. 9, 2015.
Australian Examination Report No. 1 corresponding to counterpart Int'l Appin No. AU 2014200584 dated Jun. 15, 2015.
European Office Action corresponding to counterpart Int'l Appln No. EP 13 180 881.8 dated Jun. 19, 2015.
European Office Action corresponding to counterpart Int'l Appln No. EP 14 157 195.0 dated Jul. 2, 2015.
Extended European Search Report corresponding to counterpart Int'l Appln No. EP 12 19 6902.6 dated Aug. 6, 2015.
Extended European Search Report corresponding to counterpart Int'l Appln No. EP 14 15 2060.1 dated Aug. 14, 2015.
Chinese Office Action corresponding to counterpart Int'l Appln No. CN 201210129787.2 dated Aug. 24, 2015.
European Communication corresponding to counterpart Int'l Appln. No. EP 13 17 6895.4 dated Nov. 5, 2015.
Chinese First Office Action corresponding to counterpart Int'l Appln. No. CN 201210544552 dated Nov. 23, 2015.
Chinese First Office Action corresponding to counterpart Int'l Appln. No. CN 201210545228 dated Nov. 30, 2015.
Japanese Office Action corresponding to counterpart Int'l Appln. No. JP 2014-216989 dated Sep. 11, 2015.
Canadian First Office Action corresponding to counterpart Int'l Appln. No. CA 2,686,105 dated Sep. 17, 2015.
Japanese Office Action corresponding to counterpart Int'l Appln. No. JP 2012-040188 dated Oct. 21, 2015.
Extended European Search Report corresponding to counterpart Int'l Appln. No. EP 15 18 0491.1 dated Dec. 9, 2015.
Extended European Search Report corresponding to counterpart Int'l Appln. No. EP 15 18 3819.0 dated Dec. 11, 2015.
Canadian Office Action corresponding to counterpart Int'l Appln. No. CA 2,697,819 dated Jan. 6, 2016.
Canadian Office Action corresponding to counterpart Int'l Appln. No. CA 2,696,419 dated Jan. 14, 2016.
European Office Action corresponding to counterpart Int'l Appln. No. EP 12 19 8776.2 dated Jan. 19, 2016.
Extended European Search Report corresponding to counterpart Int'l Appln. No. EP 15 17 4146.9 dated Jan. 20, 2016.
Chinese First Office Action corresponding to counterpart Int'l Appln. No. CN 201310353628.5 dated Jan. 25, 2016.
Extended European Search Report corresponding to counterpart Int'l Appln. No. EP 12 19 6912.5 dated Feb. 1, 2016.
Japanese Office Action corresponding to counterpart Int'l Appln. No. JP 2012-098903 dated Feb. 22, 2016.
Extended European Search Report corresponding to counterpart Int'l Appln. No. EP 12 19 8753.1 dated Feb. 24, 2016.
Chinese First Office Action corresponding to counterpart Int'l Appln. No. CN 201410449019.4 dated Mar. 30, 2016.
Extended European Search Report corresponding to counterpart Int'l Appln. No. EP 16150232.3, dated Apr. 12, 2016.
European Office Action corresponding to counterpart Int'l Appln. No. EP 11 18 3256.4 dated Apr. 20, 2016.
Australian Examination Report No. 1 corresponding to counterpart Int'l Appln. No. AU 2012244169 dated May 10, 2016.
European Office Action corresponding to counterpart Int'l Appln. No. EP 10 25 0715.9 dated May 12, 2016.
Chinese First Office Action corresponding to counterpart Int'l Appln. No. CN 201410778512.0 dated May 13, 2016.
Australian Examination Report No. 1 corresponding to counterpart Int'l Appln. No. AU 2012227358 dated May 16, 2016.
Japanese Office Action corresponding to counterpart Int'l Appln. No. JP 2012-040188 dated May 17, 2016.
Australian Examination Report No. 1 corresponding to counterpart Int'l Appln. No. AU 2012244380 dated May 20, 2016.
Extended European Search Report corresponding to counterpart European Appln. No. EP 17 17 8528.0 dated Oct. 13, 2017.
Australian Examination Report No. 1 corresponding to counterpart Australian Appln. No. AU 2013234420 dated Oct. 24, 2017.
Japanese Office Action corresponding to counterpart Japanese Appln. No. JP 2013-175379 dated Oct. 20, 2017.
Japanese Office Action corresponding to counterpart Japanese Appln. No. JP 2013-147701 dated Oct. 27, 2017.
Extended European Search Report corresponding to counterpart European Appln. No. EP 17 17 5656.2 dated Nov. 7, 2017.
Japanese Office Action corresponding to counterpart Japanese Appln. No. JP 2014-009738 dated Nov. 14, 2017.
European Office Action corresponding to counterpart European Appln. No. EP 13 17 3986.4 dated Nov. 29, 2017.
Japanese Office Action corresponding to counterpart Japanese Appln. No. JP 2017-075975 dated Dec. 4, 2017.
European Office Action corresponding to counterpart European Appln. No. EP 13 19 79585 dated Dec. 11, 2017.
European Office Action corresponding to Patent Application EP 16 16 6367.9 dated Dec. 11, 2017.
Chinese First Office Action corresponding to Patent Application CN 201610279682.3 dated Jan. 10, 2018.
Japanese Office Action corresponding to Patent Application JP 2013-154561 dated Jan. 15, 2018.
Australian Examination Report No. 1 corresponding to Patent Application AU 2017225037 dated Jan. 23, 2018.
Japanese Office Action corresponding to Patent Application JP 2013-229471 dated May 1, 2018.
Canadian Office Action corresponding to Patent Application CA 2,790,743 dated May 14, 2018.
European Office Action corresponding to Patent Application EP 14 15 7195.0 dated Jun. 12, 2018.
Australian Examination Report No. 1 corresponding to counterpart Int'l Appln. No. AU 2014227480 dated May 21, 2016.
Australian Examination Report No. 1 corresponding to counterpart Int'l Appln. No. AU 2012254977 dated May 30, 2016.
Extended European Search Report corresponding to counterpart Int'l Appln. No. EP 16 15 3647.9 dated Jun. 3, 2016.
Extended European Search Report corresponding to EP 13 17 7437.4, completed Sep. 11, 2013 and dated Sep. 19, 2013; (6 pp).
Extended European Search Report corresponding to EP 13 17 7441.6, completed Sep. 11, 2013 and dated Sep. 19, 2013; (6 pp).
Extended European Search Report corresponding to EP 07 86 1534.1, completed Sep. 20, 2013 and dated Sep. 30, 2013; (5 pp).
Extended European Search Report corresponding to EP 13 18 3876.5, completed Oct. 14, 2013 and dated Oct. 24, 2013; (5 pp).
Extended European Search Report corresponding to EP 13 17 1856.1, completed Oct. 29, 2013 and dated Nov. 7, 2013; (8 pp).
Extended European Search Report corresponding to EP 13 18 0373.6, completed Oct. 31, 2013 and dated Nov. 13, 2013; (7 pp).
Extended European Search Report corresponding to EP 13 18 0881.8, completed Nov. 5, 2013 and dated Nov. 14, 2013; (6 pp).

(56) References Cited

OTHER PUBLICATIONS

Extended European Search Report corresponding to EP 13 17 6895.4, completed Nov. 29, 2013 and dated Dec. 12, 2013; (5 pp).
Extended European Search Report corresponding to EP 13 18 2911.1, completed Dec. 2, 2013 and dated Dec. 16, 2013; (8 pp).
Extended European Search Report corresponding to EP 10 25 1795.0, completed Dec. 11, 2013 and dated Dec. 20, 2013; (6 pp).
Extended European Search Report corresponding to EP 13 18 7911.6, completed Jan. 22, 2014 and dated Jan. 31, 2014; (8 pp).
Extended European Search Report corresponding to EP 13 19 2123.1, completed Jan. 30, 2014 and dated Feb. 10, 2014; (8 pp).
Extended European Search Report corresponding to EP 13 19 2111.6, completed Feb. 13, 2014 and dated Feb. 27, 2014; (10 pp).
Extended European Search Report corresponding to EP 13 19 5919.9, completed Feb. 10, 2014 and dated Mar. 3, 2014; (7 pp).
Extended European Search Report corresponding to EP 08 72 6500.5, completed Feb. 20, 2014 and dated Mar. 3, 2014; (7 pp).
Extended European Search Report corresponding to EP 13 19 5019.8, completed Mar. 14, 2014 and dated Mar. 24, 2014; (7 pp).
Extended European Search Report corresponding to EP 13 19 7958.5, completed Apr. 4, 2014 and dated Apr. 15, 2014; (8 pp).
Extended European Search Report corresponding to EP 13 19 4995.0, completed Jun. 5, 2014 and dated Jun. 16, 2014; (5 pp).
Extended European Search Report corresponding to EP 14 15 7195.0, completed Jun. 5, 2014 and dated Jun. 18, 2014; (9 pp).
Extended European Search Report corresponding to EP 14 15 6342.9, completed Jul. 22, 2014 and dated Jul. 29, 2014; (8 pp).
Extended European Search Report corresponding to EP 13 19 6816.6, completed Mar. 28, 2014 and dated Apr. 9, 2014; (9 pp).
Extended European Search Report corresponding to EP 12 19 1035.0, completed Jan. 11, 2013 and dated Jan. 18, 2013; 7 pp.
Extended European Search Report corresponding to EP 12 19 6904.2, completed Mar. 28, 2013 and dated Jul. 26, 2013; 8 pp.
Extended European Search Report corresponding to EP 12 19 8749.9, completed May 21, 2013 and dated May 31, 2013; 8 pp.
Extended European Search Report corresponding to EP 07 00 5842.5, completed May 13, 2013 and dated May 29, 2013; 7 pages.
Extended European Search Report corresponding to EP 12 19 8776.2, completed May 16, 2013, and dated May 27, 2013; 8 pages.
Extended European Search Report corresponding to EP 13 15 6297.7, completed Jun. 4, 2013 and dated Jun. 13, 2013; 7 pages.
Extended European Search Report corresponding to EP 13 17 3985.6, completed Aug. 19, 2013 and dated Aug. 28, 2013; 6 pages.
Extended European Search Report corresponding to EP 13 17 3986.4, completed Aug. 20, 2013 and dated Aug. 29, 2013; 7 pages.
International Search Report corresponding to European Application No. EP 05 02 25853, completed on Jan. 25, 2006 and dated Feb. 3, 2006; 4 pages.
International Search Report corresponding to European Application No. EP 06 00 4598, completed on Jun. 22, 2006; 2 pages.
International Search Report corresponding to European Application No. EP 06 01 6962.0, completed on Jan. 3, 2007 and dated Jan. 11, 2007; 10 pages.
International Search Report corresponding to International Application No. PCT/US05/36740, completed on Feb. 20, 2007 and dated Mar. 23, 2007; 8 pages.
International Search Report corresponding to International Application No. PCT/US2007/022713, completed on Apr. 21,2008 and dated May 15, 2008; 1 page.
International Search Report corresponding to International Application No. PCT/US2008/002981, completed on Jun. 9, 2008 and dated Jun. 26, 2008; 2 pages.
International Search Report corresponding to European Application No. EP 08 25 1779, completed on Jul. 14, 2008 and dated Jul. 23, 2008; 5 pages.
International Search Report corresponding to European Application No. EP 08 25 19893, completed on Mar. 11, 2010 and dated Mar. 24, 2010; 6 pages.
International Search Report corresponding to European Application No. EP 10 25 0639.1, completed on Jun. 17, 2010 and dated Jun. 28, 2010; 7 pages.
International Search Report corresponding to European Application No. EP 10 25 0715.9, completed on Jun. 30, 2010 and dated Jul. 20, 2010; 3 pages.
International Search Report corresponding to European Application No. EP 05 80 4382.9, completed on Oct. 5, 2010 and dated Oct. 12, 2010; 3 pages.
International Search Report corresponding to European Application No. EP 10 25 1437.9, completed on Nov. 22, 2010 and dated Dec. 16, 2010; 3 pages.
International Search Report corresponding to European Application No. EP 09 25 28975, completed on Feb. 7, 2011 and dated Feb. 15, 2011; 3 pages.
International Search Report corresponding to European Application No. EP 10 25 06425, completed on Mar. 25, 2011 and dated Apr. 4, 2011; 4 pages.
International Search Report corresponding to European Application No. EP 11 18 8309.6, completed on Dec. 15, 2011 and dated Jan. 12, 2012; 3 pages.
International Search Report corresponding to European Application No. EP 12 15 2229.6, completed on Feb. 23, 2012 and dated Mar. 1, 2012; 4 pages.
International Search Report corresponding to European Application No. EP 12 15 0511.9, completed on Apr. 16, 2012 and dated Apr. 24, 2012; 7 pages.
International Search Report corresponding to European Application No. EP 12 15 2541.4, completed on Apr. 23, 2012 and dated May 3, 2012; 10 pages.
International Search Report corresponding to European Application No. EP 12 16 5609.4, completed on Jul. 5, 2012 and dated Jul. 13, 2012; 8 pages.
International Search Report corresponding to European Application No. EP 12 15 8861.0, completed on Jul. 17, 2012 and dated Jul. 24, 2012; 9 pages.
International Search Report corresponding to European Application No. EP 12 16 58785, completed on Jul. 24, 2012 and dated Aug. 6, 2012; 8 pages.

* cited by examiner

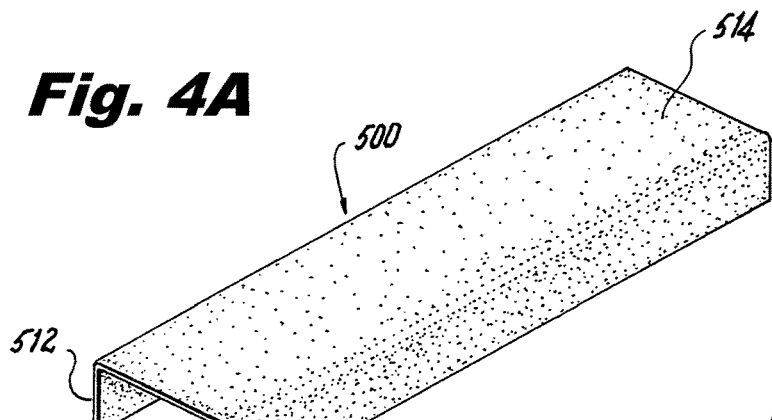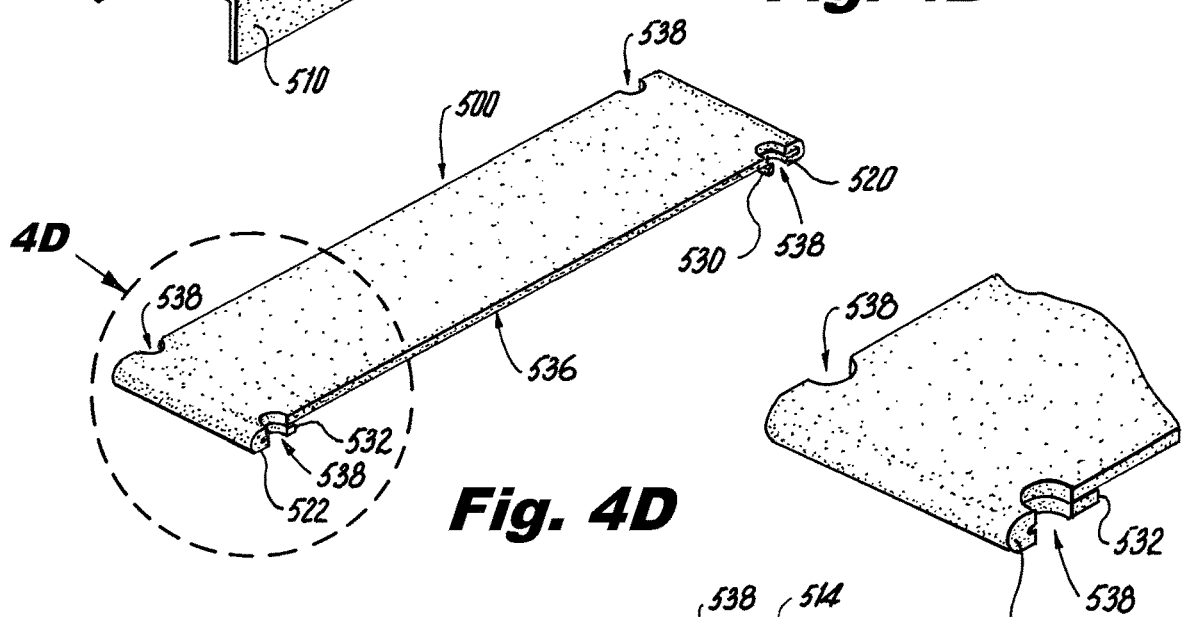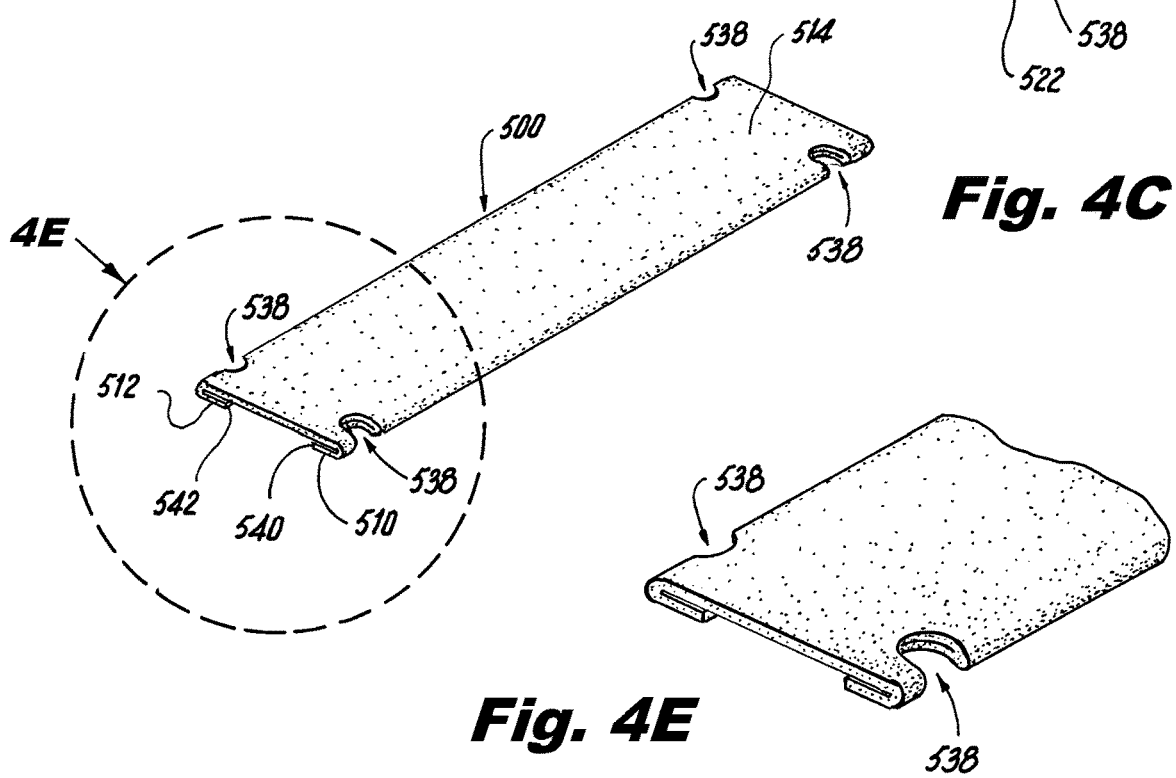

FOLDED BUTTRESS FOR USE WITH A SURGICAL APPARATUS

CROSS-REFERENCE TO RELATED APPLICATIONS

This application is a continuation which claims the benefit of and priority to U.S. patent application Ser. No. 15/201,952, filed Jul. 5, 2016, which is a continuation which claims the benefit of and priority to U.S. patent application Ser. No. 13/713,261, filed Dec. 13, 2012 (now U.S. Pat. No. 9,402,627), the entire contents of each of which are incorporated herein by reference.

BACKGROUND

Technical Field

The present disclosure relates to surgical stapling apparatus including surgical buttresses which can be releasably attached to the surgical stapling apparatus, and in particular, surgical buttresses folded and contoured so as to remain securely attached.

Background of Related Art

Surgical stapling apparatus are employed by surgeons to sequentially or simultaneously apply one or more rows of fasteners, e.g., staples or two-part fasteners, to body tissue for the purpose of joining segments of body tissue together. Such apparatus generally include a pair of jaws or finger-like structures between which the body tissue to be joined is placed. When the stapling apparatus is actuated, or "fired", longitudinally moving firing bars contact staple drive members in one of the jaws. The staple drive members push the surgical staples through the body tissue and into an anvil in the opposite jaw which forms the staples. If tissue is to be removed or separated, a knife blade can be provided in the jaws of the apparatus to cut the tissue between the lines of staples.

It is known to rely on a knife blade for cutting off some portion of the surgical buttress to affect release. A secondary material or mounting structure may be employed in addition to the surgical buttress (e.g., sutures) to provide attachment of the surgical buttress to the surgical stapling apparatus. Typically, firing forces are increased with each material that must be transected by the knife blade in order to release the surgical buttress.

It would be desirable to provide a surgical buttress that may be releasably secured to a surgical stapling apparatus without the need for a secondary material or mounting structure, and without the need for a knife blade to cut the secondary material or mounting structure to release the surgical buttress from the surgical stapling apparatus, thereby resulting in the use of fewer materials and lower firing forces. It would also be desirable to provide a surgical buttress having greater structural integrity and rigidity without adversely effecting a firing sequence of the surgical stapling apparatus.

SUMMARY

According to one aspect of the present disclosure, an end effector for use with a surgical apparatus wherein the end effector comprises a staple cartridge having a tissue contacting surface defining a central longitudinal slot and an anvil plate having a tissue contacting surface defining a central longitudinal slot. A folded surgical buttress configured to overlie each of the tissue contacting surfaces of the staple cartridge and anvil plate and configured to retain the surgical buttress to the tissue contacting surfaces of each of the staple cartridge and anvil plate. The surgical buttress having a first longitudinal portion, a second longitudinal portion, and middle longitudinal portion between the first and second longitudinal portions, wherein the middle longitudinal portion is folded and configured to fit within the central longitudinal slot of each of the staple cartridge and anvil plate. Preferably, the middle longitudinal portion is substantially V-shaped.

In an alternate embodiment, the surgical buttress of the staple cartridge and anvil plate each define a bottom surface, and a proximal portion with a proximal edge, wherein the proximal portion is folded in the direction of the bottom surface such that the proximal edge is adjacent the bottom surface of surgical buttress. The surgical buttress of the staple cartridge and anvil plate each have a distal portion with a distal edge, wherein the distal portion is folded in the direction of the bottom surface such that the distal edge is adjacent the bottom surface of surgical buttress.

In another aspect of the present disclosure, a staple cartridge for use with a surgical stapling apparatus, the staple cartridge comprising a cartridge body including a tissue contacting surface defining a plurality of staple retaining slots and having a central longitudinal slot and a staple disposed within each staple retaining slot of the cartridge body. A folded surgical buttress is configured to overlie each of the tissue contacting surfaces of the staple cartridge and anvil plate and configured to retain the surgical buttress to the tissue contacting surfaces of each of the staple cartridge and anvil plate. The surgical buttress has a first longitudinal portion, a second longitudinal portion and middle longitudinal portion between the first and second longitudinal portions, wherein the middle longitudinal portion is folded and configured to fit within the central longitudinal slot of each of the staple cartridge and anvil plate. Preferably, the middle longitudinal portion is substantially V-shaped.

In an alternate embodiment, the surgical buttress of the staple cartridge defines a bottom surface, and includes a proximal portion with a proximal edge, wherein the proximal portion is folded in the direction of the bottom surface such that the proximal edge is adjacent the bottom surface of surgical buttress. The surgical buttress of the staple cartridge further includes a distal portion with a distal edge, wherein the distal portion is folded in the direction of the bottom surface such that the distal edge is adjacent the bottom surface of surgical buttress.

In another aspect of the present disclosure, a surgical stapling apparatus, comprising a housing and an end effector being secured to the housing having a staple cartridge assembly having a tissue contacting surface and an anvil assembly having a tissue contacting surface, each of the staple cartridge assembly and anvil assembly having a central longitudinal slot. A folded surgical buttress is configured to overlie each of the tissue contacting surfaces of the staple cartridge and anvil plate and configured to retain the surgical buttress to the tissue contacting surfaces of each of the staple cartridge and anvil plate. The surgical buttress has a first longitudinal portion, a second longitudinal portion and middle longitudinal portion between the first and second longitudinal portions, wherein the middle longitudinal portion is folded and configured to fit within the central longitudinal slot of each of the staple cartridge and anvil plate. Preferably, the middle longitudinal portion is substantially V-shaped.

BRIEF DESCRIPTION OF THE DRAWINGS

Various embodiments of the presently disclosed interlocking buttress retention systems are disclosed herein with reference to the drawings, wherein:

FIG. 4A is a perspective view of an alternate embodiment of a surgical buttress according to the present disclosure;

FIG. 4B is a perspective view of another alternate embodiment of a surgical buttress according to the present disclosure;

FIG. 4C is a perspective view of yet another alternate embodiment of the surgical buttress according to the present disclosure;

FIG. 4D is an enlarged area of detail depicted in FIG. 4B;

FIG. 4E is an enlarged area of detail depicted in FIG. 4C;

DETAILED DESCRIPTION OF THE EMBODIMENTS

Figure 1:
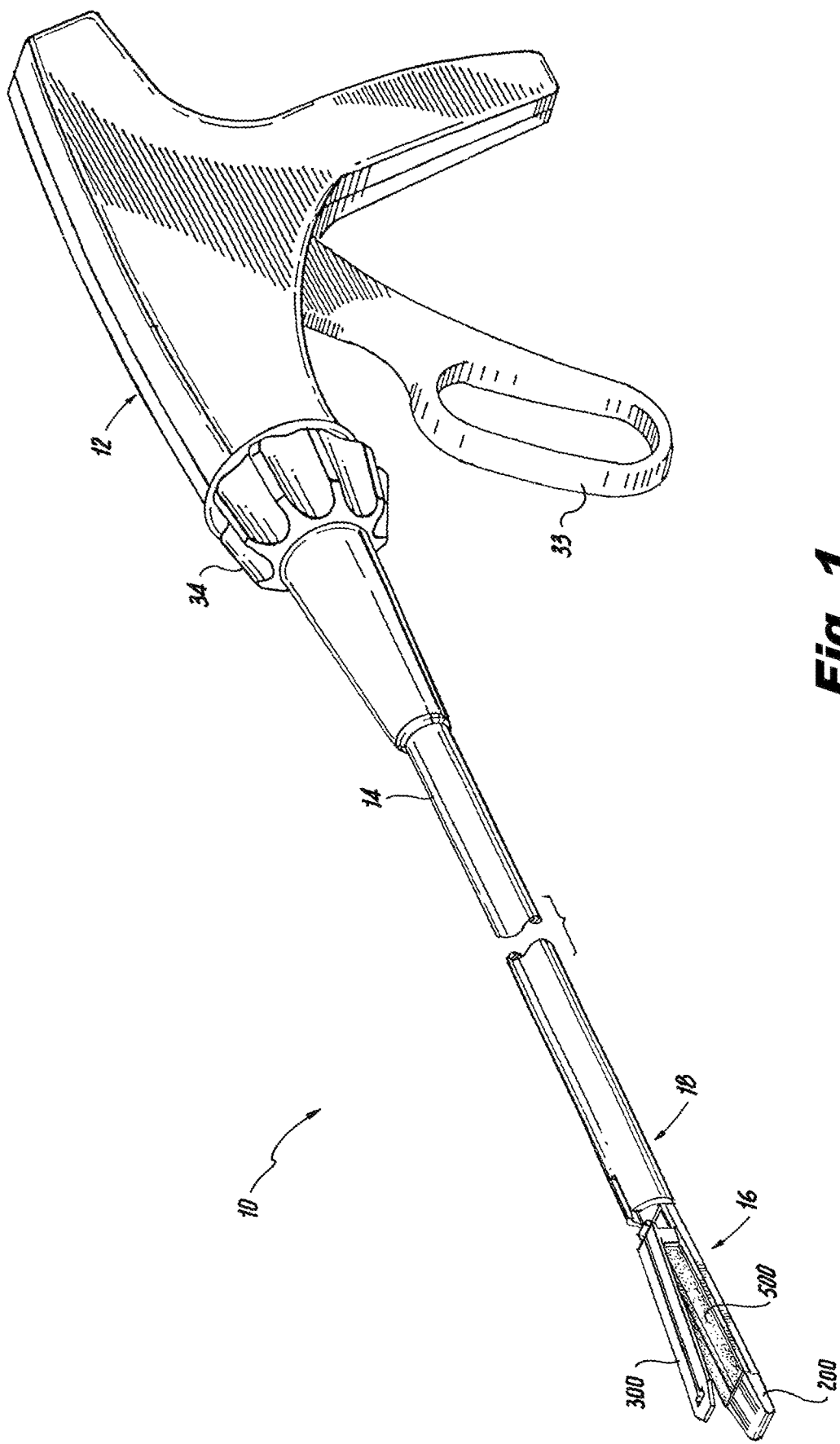
FIG. 1 is a perspective view of a surgical stapling apparatus according to an embodiment of the present disclosure.

Various exemplary embodiments of the present disclosure are discussed herein below in terms of surgical buttresses for use with surgical stapling apparatus. The surgical buttresses described herein may be used in sealing a wound by approximating the edges of wound tissue between a staple cartridge and an anvil plate of a surgical stapling apparatus which contains at least one surgical buttress. The at least one surgical buttress is releasably disposed onto a tissue contacting surface of surgical stapling apparatus by being configured to contour to the shape of surgical stapling apparatus. This allows the surgical buttress to remain securely atop the tissue contacting surface without the need for additional fasteners, sutures or similar structures. Firing of the surgical stapling apparatus forces legs of at least one staple to pass through an opening on the staple cartridge, the tissue, and the openings on the anvil plate to secure the surgical buttress to the tissue, to secure the adjoining tissue to one another, and to seal the tissue. The firing force of the staple releases the surgical buttress from the tissue contacting surface. Thus, the present disclosure describes surgical buttresses, surgical stapling apparatus supporting said surgical buttresses, and methods and mechanisms for using the same.

It should be understood that a variety of surgical stapling apparatus may be utilized with a surgical buttress of the present disclosure. For example, linear stapler configurations may be utilized, such as, for example staplers with Tri-Staple Technology™, available through Covidien, which maintain a principal place of business at 555 Long Wharf Drive, North Haven, Conn. 06511, and transverse anastomosis staplers, such as, for example, EEA™, CEEA™, GIA™, EndoGIA™, and TA™ staplers, also available through Covidien. It should also be appreciated that the principles of the present disclosure are equally applicable to surgical staplers having alternate configurations, such as, for example, end-to-end anastomosis staplers having a circular cartridge and anvil (see, e.g., commonly owned U.S. Pat. No. 5,915,616, entitled "Surgical Fastener Applying Apparatus," the entire content of which is incorporated herein by this reference); laparoscopic staplers (see, e.g., commonly owned U.S. Pat. Nos. 6,330,965 and 6,241,139, each entitled "Surgical Stapling Apparatus," the entire contents of each of which being incorporated herein by this reference); and transverse anastomosis staplers (see, e.g., commonly owned U.S. Pat. Nos. 5,964,394 and 7,334,717, each entitled "Surgical Fastener Applying Apparatus", the entire contents of each of which being incorporated herein by this reference).

Embodiments of the presently disclosed surgical buttress and surgical stapling apparatus will now be described in detail with reference to the drawing figures wherein like reference numerals identify similar or identical elements. In the following discussion, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is further from the clinician during proper use. As used herein, the term "patient" should be understood as referring to a human subject or other animal, and the term "clinician" should be understood as referring to a doctor, nurse, or other care provider and may include support personnel.

Referring now to FIG. 1, there is disclosed an exemplary surgical stapling apparatus or surgical stapler 10 for use in stapling tissue and applying a buttress material or surgical buttress to the tissue. An example of this type of surgical stapling instrument is disclosed in U.S. Pat. No. 7,128,253, the entire disclosure of which is incorporated by reference herein.

Surgical stapling apparatus 10 generally includes a handle 12 having an elongate tubular member 14 extending distally from handle 12. An end effector assembly 16 is mounted on a distal end 18 of elongate tubular member 14. End effector assembly 16 includes a first jaw or staple cartridge assembly 200 configured to receive a staple cartridge 32 therein and a second jaw or anvil assembly 300. End effector assembly 16 may be permanently affixed to elongate tubular member 14 or may be detachable and thus replaceable with a new end effector assembly 16. In addition to a replaceable end effector assembly or as an alternative thereto, the cartridge assembly 200 can be removable and replaceable. One of staple cartridge assembly 200 and anvil assembly 300 is movably mounted at distal end 18 of end effector assembly 16, and is movable between an open position spaced apart from one another to a closed position substantially adjacent to one another. Anvil assembly 300 supports an anvil plate 302 and may be fabricated from a metal material, including and not limited to stainless steel, titanium, titanium alloy, and the like. The tissue contacting surface of staple cartridge 32 may be fabricated from a material other than metal, including and not limited to plastic, thermoplastic, resin, polycarbonate, and the like.

Surgical stapling apparatus 10 further includes a trigger 33, as seen in FIG. 1, movably mounted on handle 12. Actuation of trigger 33 initially operates to move first jaw and second jaw between the open and the closed positions and simultaneously actuates surgical stapling apparatus 10 to apply lines of staples to tissue. In order to properly orient end effector assembly 16 relative to the tissue to be stapled, surgical stapling apparatus 10 is additionally provided with a rotation knob 34 mounted on handle 12. Rotation of rotation knob 34 relative to handle 12 rotates elongate tubular member 14 and end effector assembly 16 relative to handle 12 so as to properly orient end effector assembly 16 relative to the tissue to be stapled.

Figure 5:
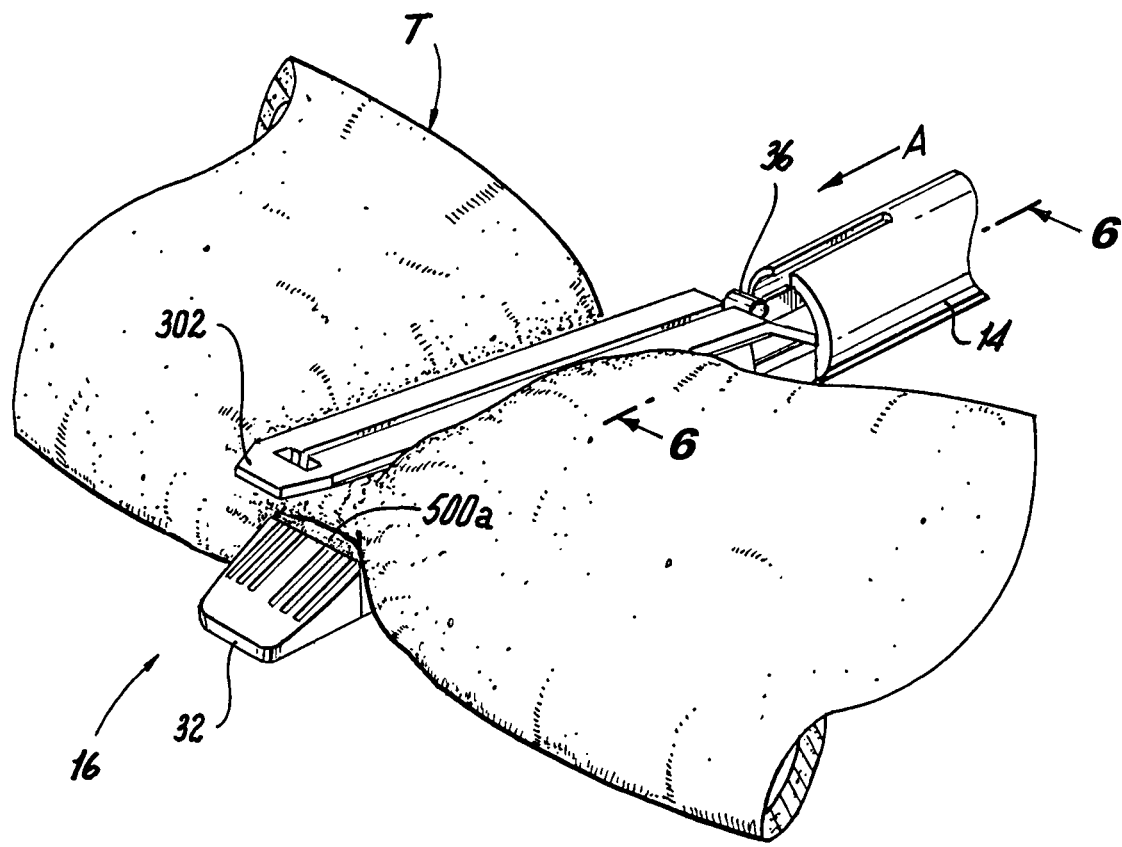
FIG. 5 is a perspective view of a distal end of the surgical stapling apparatus of FIG. 1, shown in use positioned about a tissue section.
Figure 6:
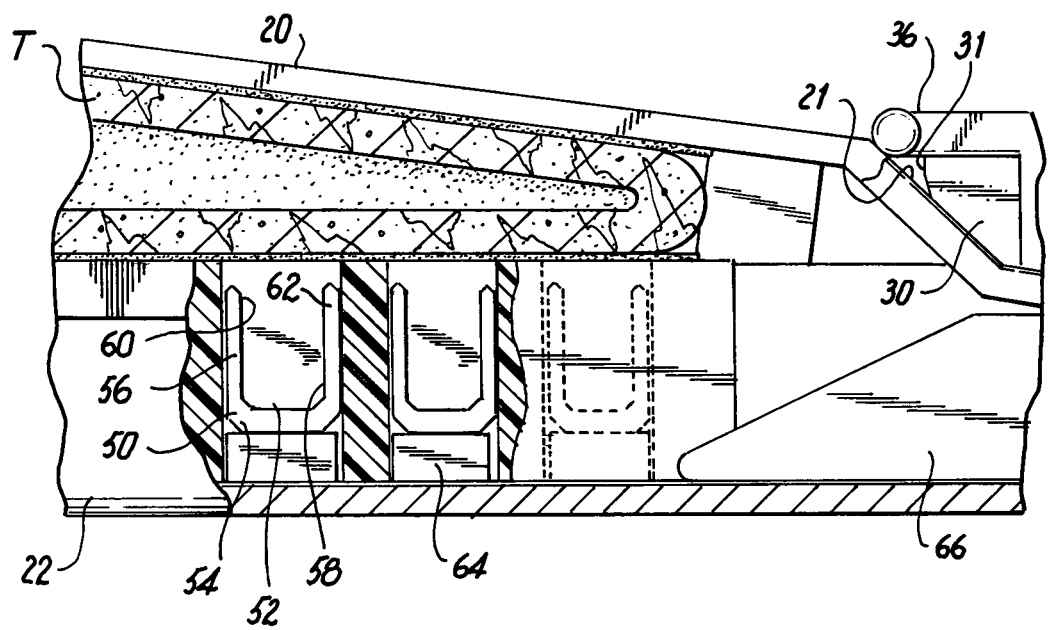
FIG. 6 is a cross-sectional view taken along line 6-6 of FIG. 5.

A driver 36, as seen in FIGS. 5 and 6, is provided to move approximate first jaw or staple cartridge assembly 200 and second jaw or anvil assembly 300 from the open position to the closed position. Driver 36 moves through a central longitudinal slot 338 (FIG. 3) formed in the anvil plate 302 of anvil assembly 300. A knife 30 with knife blade 31 is associated with driver 36 to cut tissue captured between staple cartridge assembly 200 and anvil assembly 300 as driver 36 passes through slot 338.

Reference may be made to commonly owned U.S. Pat. Nos. 5,915,616, 6,330,965, and 6,241,139, the disclosures of each of which are hereby incorporated by reference in their entirety, for a detailed discussion of the construction and operation of an exemplary surgical stapling apparatus 10.

Staple cartridge assembly 200 and/or anvil assembly 300 may be provided with a surgical buttress 500. Surgical buttress 500 is provided to reinforce and seal the lines of staples applied to tissue by surgical stapling apparatus 10. Surgical buttress 500 may be configured into any shape, size, or dimension suitable to fit any surgical stapling, fastening, or firing apparatus.

Staple cartridge assembly 200 is provided with a cartridge buttress 500*a* and anvil assembly 300 is provided with an anvil buttress 500*b* in the manners described in more detail hereinbelow. The buttresses 500*a*, 500*b* may be made from any biocompatible natural or synthetic material. The material from which the buttresses 500*a*, 500*b* are formed may be bioabsorbable or non-bioabsorbable. It should be understood that any combination of natural (including animal derived materials), synthetic, bioabsorbable and non-bioabsorbable materials may be used to form the buttress material. The buttresses 500*a*, 500*b* may be porous or non-porous, combination of porous and non-porous layers. The non-porous buttresses 500*a*, 500*b* may be utilized to retard or prevent tissue ingrowth from surrounding tissues thereby acting as an adhesion barrier and preventing the formation of unwanted scar tissue. The buttress material can be a film, foam, mesh, woven, non-woven, or other material, and can be formed by molding, blown film processes, melt blown and/or spun bonding processes.

Additional exemplary materials for surgical buttresses 500*a*, 500*b* for use with the surgical stapling devices disclosed herein are set forth in commonly assigned U.S. Pat. Nos. 5,542,594; 5,908,427; 5,964,774; and 6,045,560, and commonly assigned U.S. Application Publication Nos. 2006/0085034, filed on Apr. 20, 2006; and 2006/0135992, filed on Jun. 22, 2006, the entire contents of each of which is incorporated herein by reference. The buttress material may be formed as described in U.S. application Ser. No. 13/293,215 (now U.S. Application Publication No. 2013/0123816), the entire disclosure of which is hereby incorporated by reference herein.

Figure 2:
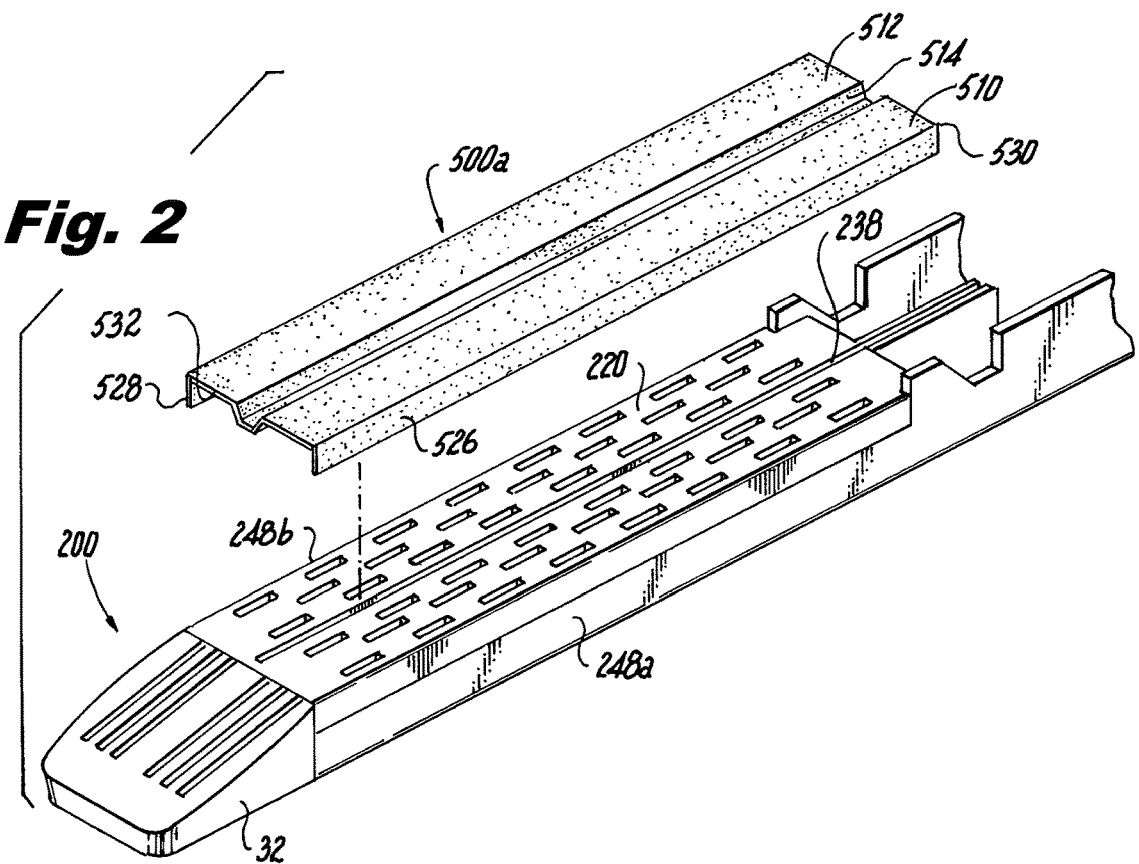
FIG. 2 is a perspective view, with parts separated, of a staple cartridge assembly of the surgical stapling apparatus of FIG. 1, illustrating an embodiment according to the present disclosure.
Figure 3:
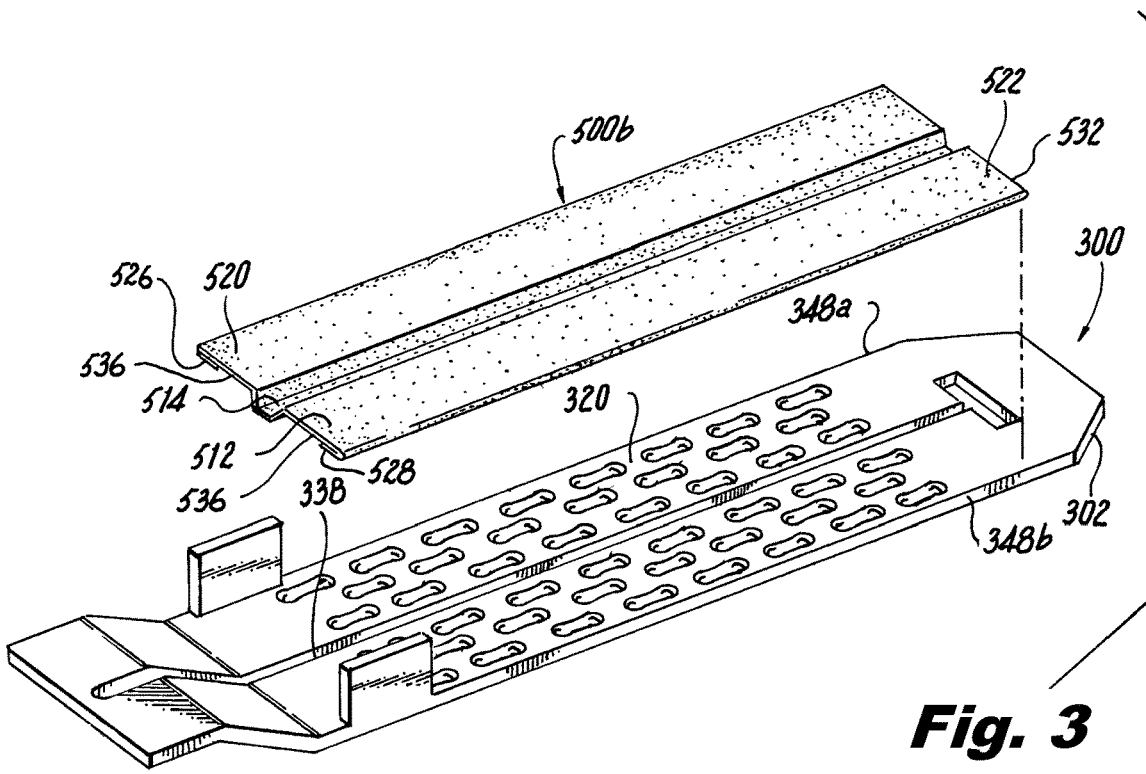
FIG. 3 is a perspective view, with parts separated, of an anvil assembly of the surgical stapling apparatus of FIG. 1, illustrating an embodiment of the present disclosure.

As illustrated in FIGS. 2 and 3, surgical buttress 500 is releasably attached to the inwardly facing or tissue contacting surfaces 220, 320 of the staple cartridge 32 and/or the anvil plate 302. The surgical buttress 500 is folded and configured to contour to the shape of the respective staple cartridge 32 and anvil plate 302. Configuring the surgical buttress 500 to take the shape of the staple cartridge 32 or anvil plate 302 allows the surgical buttress 500 to secure to the respective tissue contacting surfaces prior to firing of the stapling apparatus 10. The folded sections also provide stability for the buttress while the instrument is used, and as tissue is grasped, the instrument is manipulated, etc.

With reference to FIG. 2, cartridge buttress 500*a* of staple cartridge assembly 200 is operatively secured to a tissue contacting surface 220 of staple cartridge 32. Cartridge buttress 500*a* has a first longitudinal portion 510, a second longitudinal portion 512, and a middle longitudinal portion 514 between the first and second longitudinal portions 510, 512. The middle longitudinal portion 514 is folded and contoured to fit firmly within a central longitudinal slot 238 of staple cartridge. In this embodiment, the first and second longitudinal portions 510, 512 remain atop the tissue contacting surface 220 of staple cartridge. The middle longitudinal portion 514 is substantially V-shaped or U-shaped such that a longitudinal gap exists along the plane defined by the first and second longitudinal portions 510, 512. Stated differently, cartridge buttress 500*a* includes a first condition wherein cartridge buttress 500*a* is substantially planar, and a second condition wherein the planar cartridge buttress 500*a* is folded along its longitudinal axis to define a middle longitudinal portion 514 that is substantially V-shaped, so as to define a central longitudinally extending tab or fin. The buttress could be molded in, or pressed into, this shape using heat and/or pressure.

Contouring the cartridge buttress 500*a* to fit within the central longitudinal slot 238 prevents the cartridge buttress 500*a* from lateral movement during use of the stapling apparatus 10. Further, the exact fit of the middle portion 514 within the central longitudinal slot 238 of the staple cartridge 32 provides friction that firmly secures the cartridge buttress 500*a* in position. The shape of the fold or folds in the buttress provides stability, and can be provided in the central portion, distal portion, proximal portion, or lateral sides of the buttress. As the knife blade 31 translates distally through central longitudinal slot 238, knife blade cuts the middle portion 514 of the cartridge buttress 500*a*, along the folded portion, further releasing the first and second longitudinal portions 510, 512 from the tissue contacting surface 220 of staple cartridge 32.

FIGS. 2 and 3 illustrate additional features of the buttresses 500*a*, 500*b* for securing the buttresses 500*a*, 500*b* to the respective tissue contacting surfaces 220, 320. As shown in FIG. 2, staple cartridge 32 has a first outer side surface 248*a* and a second outer side surface 248*b*. A first extension 526 of the cartridge buttress 500*a* extends downwardly from the first longitudinal portion 510. The first extension 526 can be formed by a folded portion that extends towards the first outer side surface 248*a* of staple cartridge 32 and is positioned adjacent thereto. Similarly, a second extension 528 of the cartridge buttress 500*a*, which can also be a folded portion of the buttress, extends downwardly from the second longitudinal portion 512 and is folded towards the second outer side surface 248*b* of staple cartridge 32 and positioned adjacent thereto. The first and second extensions 526, 528 allow for increased strength to maintain the positioning of the cartridge buttress 500*a* atop the tissue contacting surface 220 of staple cartridge 32. While the first and second extensions 526 and 528 are shown in relation to the cartridge buttress 500*a*, it is understood that the anvil buttress 500*b* may include similar features.

With reference to FIG. 3, and similar to cartridge buttress 500*a*, anvil buttress 500*b* is operatively secured to a tissue contacting surface 320 of anvil plate 302 of anvil assembly 300. Anvil buttress 500*b* is folded and contoured such that the middle portion 514 is positioned firmly within the central longitudinal slot 338 of anvil plate 302. First and second longitudinal portions 510, 512 of anvil plate 302 remain atop the tissue contacting surface 320 of anvil plate 302. Stated differently, anvil buttress 500b includes a first condition wherein anvil buttress 500b is substantially planar, and a second condition wherein the planar anvil buttress 500b is folded along its longitudinal axis to define a middle longitudinal portion 514 that is substantially V-shaped, so as to define a central longitudinally extending tab or fin.

As shown in FIG. 3, first extension 526 extends from first longitudinal portion 510 and is folded towards a bottom surface 536 of the anvil buttress 500b. The first extension 526 is folded towards the bottom surface 536 so as to lay adjacent the bottom surface 536 of first longitudinal portion 510 of anvil buttress 500b. The second extension 528 extending from second longitudinal portion 512 is folded towards the bottom surface 536 of second longitudinal portion 512 so as to lay adjacent the bottom surface 536 of anvil buttress 500b. This additional feature reinforces the anvil buttress 500b and prevents the anvil buttress 500b from tearing during tensioning. Folded portions can be provided at the lateral sides of the buttress to improve stability of the buttress on the cartridge and/or anvil members. While the first and second extensions 526 and 528 are shown in relation to the anvil buttresses 500b, in this embodiment, it is understood that the cartridge buttress 500a may include similar features.

FIGS. 4A-4C illustrate alternate embodiments. Surgical buttress 500 includes contouring corresponding to the shape of the staple cartridge 32 and/or anvil plate 302. For description purposes only reference is made to cartridge buttress 500a and staple cartridge 32, however, it is understood that similar construction is utilized for anvil buttress 500b and anvil plate 302. In the alternative, the anvil buttress 500b can be configured differently, for providing stability and tear resistance experienced at the anvil plate 302.

In FIG. 4A, the middle longitudinal portion 514 of the surgical buttress 500a in this example is substantially planar and configured to lie atop the tissue contacting surfaces 220 of the staple cartridge 32. In this embodiment, first longitudinal portion 510 of the cartridge buttress 500a is folded towards the first outer side surface 248a and is adjacent thereto. Similarly, second longitudinal portion 512 of the cartridge buttress 500a is folded towards the second outer side surface 248b and is adjacent thereto. The coupling between the first longitudinal portion 510 and the first outer side surface 280a, and between the second longitudinal surface 512 and the second outer side surface 248b prevents lateral movement of the cartridge buttress 500a and anchors the cartridge buttress 500a in position. Accordingly, the buttress 500a can have one or more longitudinal folded portions.

FIG. 4B illustrates another alternate embodiment, wherein cartridge buttress 500a defines a bottom surface 536, and cartridge buttress 500a includes a proximal portion 520 and a distal portion 522 that are folded towards the bottom surface 536. Proximal portion 520 of cartridge buttress 500a has a proximal edge 530 that is folded towards the bottom surface 536 so as to lay adjacent the bottom surface 536 of the cartridge buttress 500a. Similarly, distal portion 522 of cartridge buttress 500a has a distal edge 532 that is folded towards the bottom surface 536 so as to lay adjacent the bottom surface of the cartridge buttress 500a. The buttress has one or more folded ends. In this embodiment, the proximal and distal portions 520, 522 are adjacent the tissue contacting surface 220 of staple cartridge 32. It is contemplated that the embodiments discussed herein for both the staple cartridge 32 and anvil plate 302 can be used with well-known suture retention methods known in the art. For example, as shown in FIGS. 4B and 4D, a pair of notches 538 may be disposed within each of the folded regions of the proximal and distal portions 520, 522. The suture portion or portions, or some other kind of anchor, can be positioned in the notches. Alternatively or additionally, the buttress can be secured using adhesives or welding.

FIG. 4C illustrates yet another alternate embodiment, wherein the first and second longitudinal portions 510, 512 of cartridge buttress 500a are folded towards the bottom surface 536 of the cartridge buttress 500a. In a similar manner as described above, a first longitudinal edge 540 of first longitudinal portion 510 is folded towards the bottom surface 536 so as to lay adjacent the bottom surface of cartridge buttress 500a. A second longitudinal edge 542 of second longitudinal portion 512 is folded towards the bottom surface 536 so as to lay adjacent the bottom surface 536 of cartridge buttress 500a. In this embodiment, first and second longitudinal portions 510, 512 are adjacent the tissue contacting surface 220 of staple cartridge 32. Notches 538, shown in FIG. 4E, are disposed along the folded region. It is contemplated that the notches 538 may be positioned in varying configurations to correlate with the use of sutures well known in the art. The embodiments depicted in FIGS. 4B and 4C reinforce the cartridge buttress 500a and prevent the cartridge buttress 500a from tearing during tensioning.

The notches 538 used for retaining sutures disclosed herein are set forth in commonly assigned U.S. Provisional Patent No. 61/696,906, filed on Sep. 5, 2012 (now U.S. Pat. No. 9,693,772), the entire contents of each of which is incorporated herein by reference.

Prior to assembly, the surgical buttresses 500a, 500b may be heat formed or cold folded into the contoured shape for receipt in the respective central longitudinal slots 238, 338 of staple cartridge 32 and anvil plate 302. During assembly the surgical buttresses 500a, 500b are placed onto each of the tissue contacting surfaces 220, 320 of staple cartridge assembly 200 and anvil assembly 300, respectively. Additional sutures or fasteners well known in the art may be used to further adhere the surgical buttresses 500a, 500b to each of the tissue contacting surfaces 220, 320. Additionally, other bonding methods such as adhesives, ultrasonic welding, laser welding, solvent bonding or heat pressing may be utilized in any of the embodiments disclosed herein.

As illustrated in FIG. 5, during use of surgical stapling apparatus 10, the first jaw or staple cartridge assembly 200 and the second jaw or anvil assembly 300, having surgical buttresses 500a, 500b loaded thereon (as described above) are positioned on either side of the surgical site. Tissue contacting surfaces 220, 320 of staple cartridge assembly 200 and anvil assembly 300 are positioned adjacent layers of tissue "T" to be fastened to one another.

As shown in FIG. 6, staple cartridge assembly 200 includes surgical staples 50 positioned within individual staple retaining slots 52 of staple cartridge 32. Staples 50 are of a conventional type and include a backspan 54 having a pair of legs 56 and 58 extending from backspan 54. Legs 56 and 58 terminate in tissue penetrating tips 60 and 62, respectively. Pushers 64 are located within staple retaining slots 52 and are positioned between staples 50 and the path of a drive bar 66.

In the illustrated embodiment, surgical stapling apparatus 10 is initially actuated by movement of trigger 33 relative to handle 12 (FIG. 1) causing driver 36 to move in the direction of arrow "A" (FIG. 5), and against sloped edge 21 of anvil plate 302 thereby causing anvil assembly 300 to be moved to the closed position relative to staple cartridge assembly 200. As drive bar 66 advances distally within staple cartridge 32, drive bar 66 urges pushers 64 upwardly against backspan 54 of staples 50 driving legs 56 and 58 of staples 50 through the cartridge buttresses 500a, tissue "T", and anvil buttress 500b, towards staple forming pockets 68 in anvil plate 302 of anvil assembly 300. Tissue penetrating tips 60 and 62 of staple legs 56 and 58 are formed within staple forming pockets 68 in anvil plate 302 with backspan 54 securing surgical buttress 500 against tissue "T".

Upon full actuation of surgical stapling apparatus 10, a knife 30 (FIG. 6) associated with surgical stapling apparatus 10 and carried by driver 36 may be utilized to cut tissue "T", as well as surgical buttresses 500a, 500b between the rows of now formed staples 50. Upon movement of anvil assembly 300 to the open position, spaced apart from staple cartridge assembly 200, buttresses 500a, 500b are pulled away and released from respective tissue contacting surfaces 220, 320 of respective staple cartridge assembly 200 and anvil assembly 300.

Figure 7:
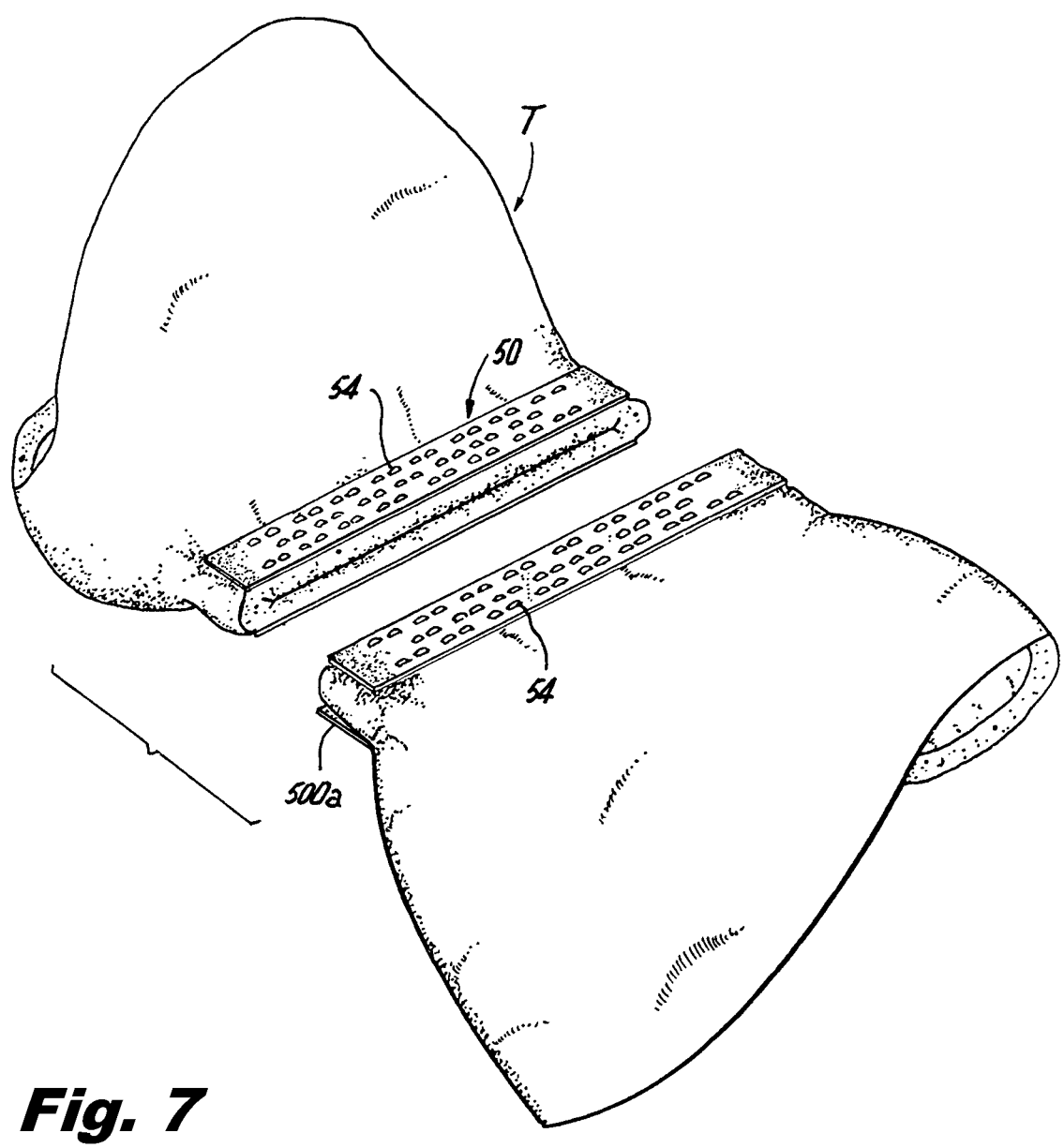
FIG. 7 is a perspective view of the stapled and divided tissue section of FIG. 5.

The resulting tissue "T", divided and stapled closed with staples 50, is illustrated in FIG. 7. Specifically, surgical buttresses 500a, 500b are secured against tissue "T" by legs 56, 58 and backspan 54 of staples 50. Thus, surgical buttresses 500a, 500b are stapled to tissue "T" thereby sealing and reinforcing the staple lines created by staples 50.

Persons skilled in the art will understand that the devices and methods specifically described herein and illustrated in the accompanying figures are non-limiting exemplary embodiments, and that the description, disclosure, and figures should be construed merely exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another exemplary embodiment without departing from the scope of the present disclosure, and that such modifications and variations are also intended to be included within the scope of the present disclosure. Accordingly, the subject matter of the present disclosure is not to be limited by what has been particularly shown and described, except as indicated by the appended claims.

What is claimed is:

1. An end effector assembly comprising:
   a staple cartridge assembly including a tissue contacting surface;
   an anvil assembly including a tissue contacting surface; and
   a surgical buttress having a top surface, a bottom surface, first and second longitudinal side portions, and proximal and distal end portions, the surgical buttress including first and second folded portions in opposed regions of the surgical buttress, the first and second folded portions disposed between the bottom surface of the surgical buttress and the tissue contacting surface of the staple cartridge assembly or the anvil assembly, the surgical buttress including first and second pairs of opposed notches, each notch of the first and second pairs of opposed notches defined in the first or second folded portion of the surgical buttress.

2. The end effector assembly of claim 1, wherein the first pair of opposed notches of the surgical buttress is defined in the proximal portion of the surgical buttress and the second pair of opposed notches is defined in the distal portion of the surgical buttress.

3. The end effector assembly of claim 1, wherein the opposed regions of the surgical buttress including the first and second folded portions are the proximal and distal portions of the surgical buttress.

4. The end effector assembly of claim 3, wherein the first folded portion of the surgical buttress includes a proximal edge of the proximal portion positioned against the bottom surface, and the second folded portion of the surgical buttress includes a distal edge of the distal portion positioned against the bottom surface.

5. The end effector assembly of claim 1, wherein the opposed regions of the surgical buttress including the first and second folded portions are the first and second longitudinal side portions of the surgical buttress.

6. The end effector assembly of claim 5, wherein the first folded portion of the surgical buttress includes a first longitudinal edge of the first longitudinal side portion positioned against the bottom surface, and the second folded portion of the surgical buttress includes a second longitudinal edge of the second longitudinal side portion positioned against the bottom surface.

7. A staple cartridge assembly comprising:
   a staple cartridge including a tissue contacting surface; and
   a surgical buttress having a top surface, a bottom surface, first and second longitudinal side portions, and proximal and distal end portions, the surgical buttress including first and second folded portions in opposed regions of the surgical buttress, the first and second folded portions disposed between the bottom surface of the surgical buttress and the tissue contacting surface of the staple cartridge, the surgical buttress including first and second pairs of opposed notches, each notch of the first and second pairs of opposed notches defined in the first or second folded portion of the surgical buttress.

8. The staple cartridge assembly of claim 7, wherein the first pair of opposed notches of the surgical buttress is defined in the proximal portion of the surgical buttress and the second pair of opposed notches is defined in the distal portion of the surgical buttress.

9. The staple cartridge assembly of claim 7, wherein the opposed regions of the surgical buttress including the first and second folded portions are the proximal and distal portions of the surgical buttress.

10. The staple cartridge assembly of claim 9, wherein the first folded portion of the surgical buttress includes a proximal edge of the proximal portion positioned against the bottom surface, and the second folded portion of the surgical buttress includes a distal edge of the distal portion positioned against the bottom surface.

11. The staple cartridge assembly of claim 7, wherein the opposed regions of the surgical buttress including the first and second folded portions are the first and second longitudinal side portions of the surgical buttress.

12. The staple cartridge assembly of claim 11, wherein the first folded portion of the surgical buttress includes a first longitudinal edge of the first longitudinal side portion positioned against the bottom surface, and the second folded portion of the surgical buttress includes a second longitudinal edge of the second longitudinal side portion positioned against the bottom surface.

13. An anvil assembly comprising:

an anvil plate including a tissue contacting surface; and
a surgical buttress having a top surface, a bottom surface, first and second longitudinal side portions, and proximal and distal end portions, the surgical buttress including first and second folded portions in opposed regions of the surgical buttress, the first and second folded portions disposed between the bottom surface of the surgical buttress and the tissue contacting surface of the anvil plate, the surgical buttress including first and second pairs of opposed notches, each notch of the first and second pairs of opposed notches defined in the first or second folded portion of the surgical buttress.

14. The anvil assembly of claim 13, wherein the first pair of opposed notches of the surgical buttress is defined in the proximal portion of the surgical buttress and the second pair of opposed notches is defined in the distal portion of the surgical buttress.

15. The anvil assembly of claim 13, wherein the opposed regions of the surgical buttress including the first and second folded portions are the proximal and distal portions of the surgical buttress.

16. The anvil assembly of claim 15, wherein the first folded portion of the surgical buttress includes a proximal edge of the proximal portion positioned against the bottom surface, and the second folded portion of the surgical buttress includes a distal edge of the distal portion positioned against the bottom surface.

17. The anvil assembly of claim 13, wherein the opposed regions of the surgical buttress including the first and second folded portions are the first and second longitudinal side portions of the surgical buttress.

18. The anvil assembly of claim 17, wherein the first folded portion of the surgical buttress includes a first longitudinal edge of the first longitudinal side portion positioned against the bottom surface, and the second folded portion of the surgical buttress includes a second longitudinal edge of the second longitudinal side portion positioned against the bottom surface.

* * * * *